(12) United States Patent
Michels et al.

(10) Patent No.: US 8,244,379 B2
(45) Date of Patent: Aug. 14, 2012

(54) PERICARDIUM FIXATION CONCEPTS OF EPICARDIUM PACING LEADS AND TOOLS

(75) Inventors: Koen Michels, Maastricht (NL); Jean-Luc Jansens, Merchtem (BE); Victor Duysens, Grevenbicht (NL); Paulus G. Adams, Munstergeleen (NL); Paulus Van Venrooij, Hoensbroek (NL); Markus J. C. Lazeroms, Vroenhoven-Riemst (BE); Fredric W. Lindemans, Sittard (NL)

(73) Assignee: Medtronic, Inc., Minneapolis, MN (US)

( * ) Notice: Subject to any disclaimer, the term of this patent is extended or adjusted under 35 U.S.C. 154(b) by 431 days.

(21) Appl. No.: 11/380,234

(22) Filed: Apr. 26, 2006

(65) Prior Publication Data
US 2007/0255376 A1 Nov. 1, 2007

(51) Int. Cl.
*A61N 1/05* (2006.01)
(52) U.S. Cl. .......................................... 607/130
(58) Field of Classification Search .............. 607/2, 5, 607/35, 119, 126–132
See application file for complete search history.

(56) References Cited

U.S. PATENT DOCUMENTS

| | | | | |
|---|---|---|---|---|
| 4,865,037 A | * | 9/1989 | Chin et al. | 607/2 |
| 4,884,567 A | * | 12/1989 | Elliott et al. | 606/126 |
| 4,946,457 A | | 8/1990 | Elliott | |
| 4,991,578 A | | 2/1991 | Cohen | |
| 4,998,975 A | | 3/1991 | Cohen et al. | |
| 5,033,477 A | * | 7/1991 | Chin et al. | 607/131 |
| 5,090,422 A | * | 2/1992 | Dahl et al. | 607/119 |
| 5,127,421 A | * | 7/1992 | Bush et al. | 607/130 |
| 5,249,574 A | * | 10/1993 | Bush et al. | 607/9 |
| 5,273,053 A | * | 12/1993 | Pohndorf | 607/132 |
| 5,314,462 A | * | 5/1994 | Heil et al. | 607/128 |
| 5,336,252 A | | 8/1994 | Cohen | |
| 5,618,287 A | | 4/1997 | Fogarty et al. | |
| 5,871,532 A | * | 2/1999 | Schroeppel | 607/128 |
| 5,931,810 A | * | 8/1999 | Grabek | 604/506 |
| 6,156,009 A | * | 12/2000 | Grabek | 604/117 |
| 6,162,195 A | * | 12/2000 | Igo et al. | 604/164.13 |
| 6,249,707 B1 | | 6/2001 | Kohnen et al. | |
| 6,613,062 B1 | | 9/2003 | Leckrone et al. | |
| 6,666,844 B1 | * | 12/2003 | Igo et al. | 604/115 |
| 6,837,848 B2 | | 1/2005 | Bonner et al. | |

(Continued)

OTHER PUBLICATIONS

International Search Report, PCT/US2007/066680, Oct. 10, 2007, 6 Pages.

*Primary Examiner* — Carl H Layno
*Assistant Examiner* — Luther Behringer
(74) *Attorney, Agent, or Firm* — Reed A. Duthler; Stephen W. Bauer

(57) ABSTRACT

Certain aspects of the disclosure pertain to methods and apparatus for providing positive fixation of medical components to a portion of incised pericardial tissue. Accordingly, a resilient member protrudes through an incision in the pericardium and produces a positive biasing force to adjacent pericardial tissue against a side surface of an attached body structure. The resilient member can optionally be compressed during implantation and then relaxed to thereafter provide the positive biasing force. Diverse medical components can thus be safely and reliably chronically deployed into the pericardial space, including without limitation, cardiac sensing/pacing, defibrillation and/or cardioversion electrodes, mechanical and/or metabolic sensors and the like. More than one body structure can be linked to a single medical electrical lead and the medical components can couple within and/or upon a portion of the body structure, the resilient member, and the lead in myriad configurations.

21 Claims, 25 Drawing Sheets

U.S. PATENT DOCUMENTS

| | | |
|---|---|---|
| 2003/0212446 A1 | 11/2003 | Kaplan et al. |
| 2004/0186521 A1* | 9/2004 | Rubin et al. ............... 607/5 |
| 2004/0215308 A1* | 10/2004 | Bardy et al. ............... 607/129 |
| 2005/0154370 A1 | 7/2005 | Sigg et al. |
| 2005/0165466 A1 | 7/2005 | Morris et al. |
| 2007/0255375 A1 | 11/2007 | Michels et al. |

* cited by examiner

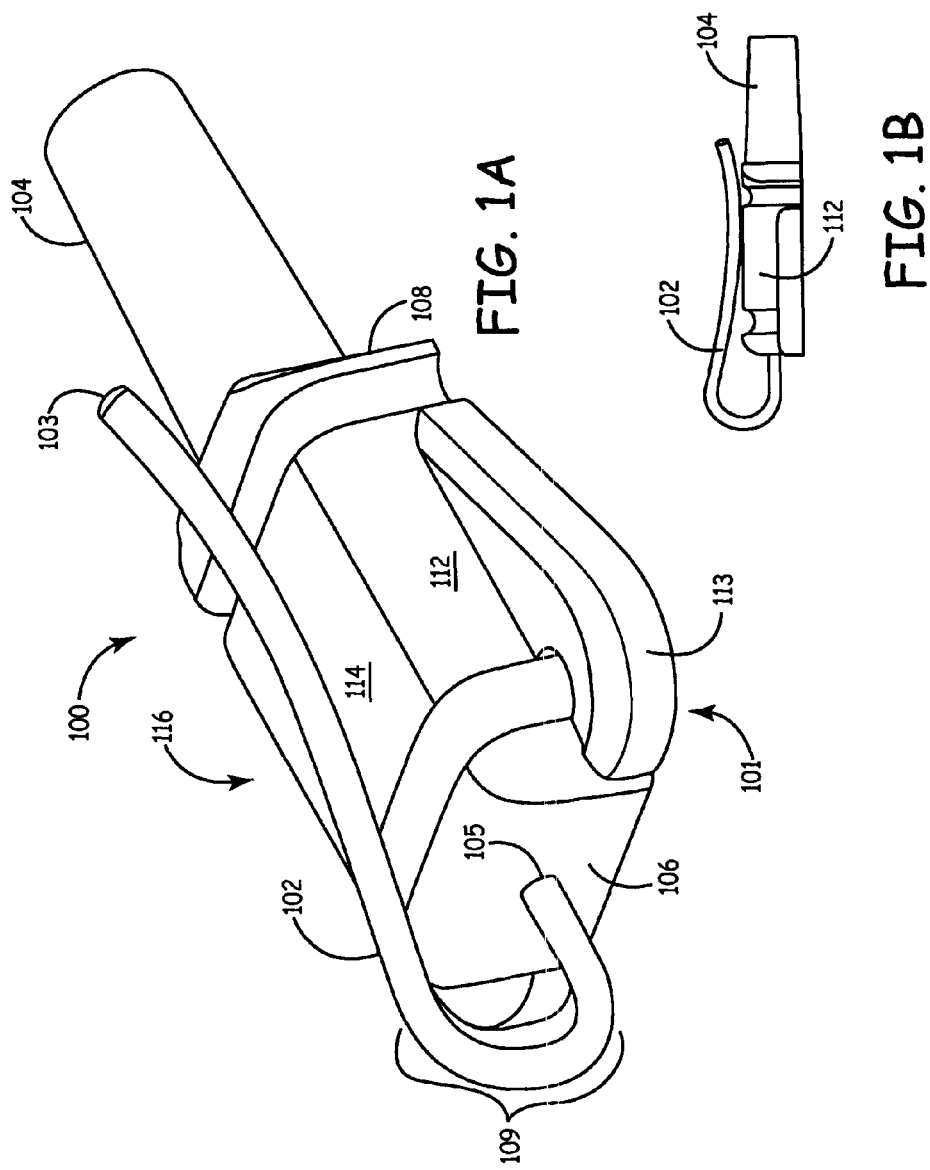

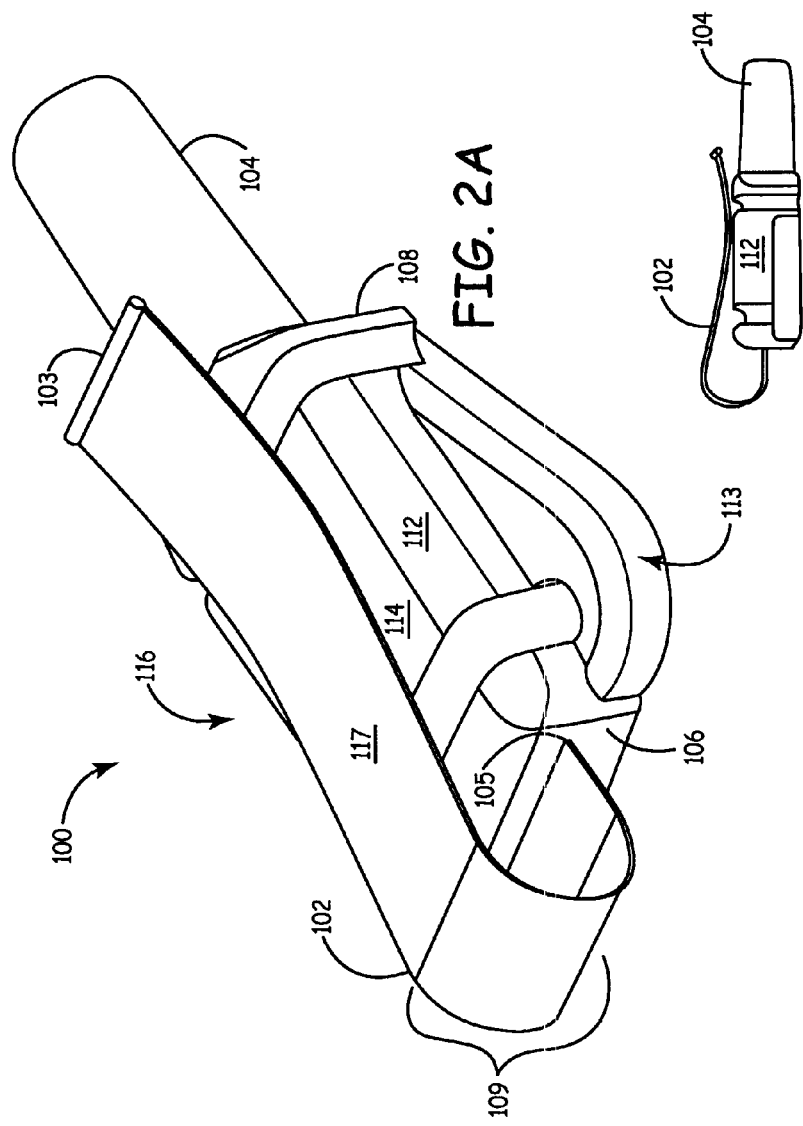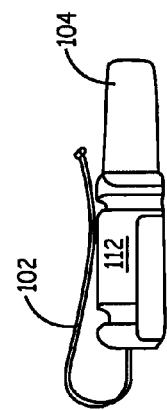

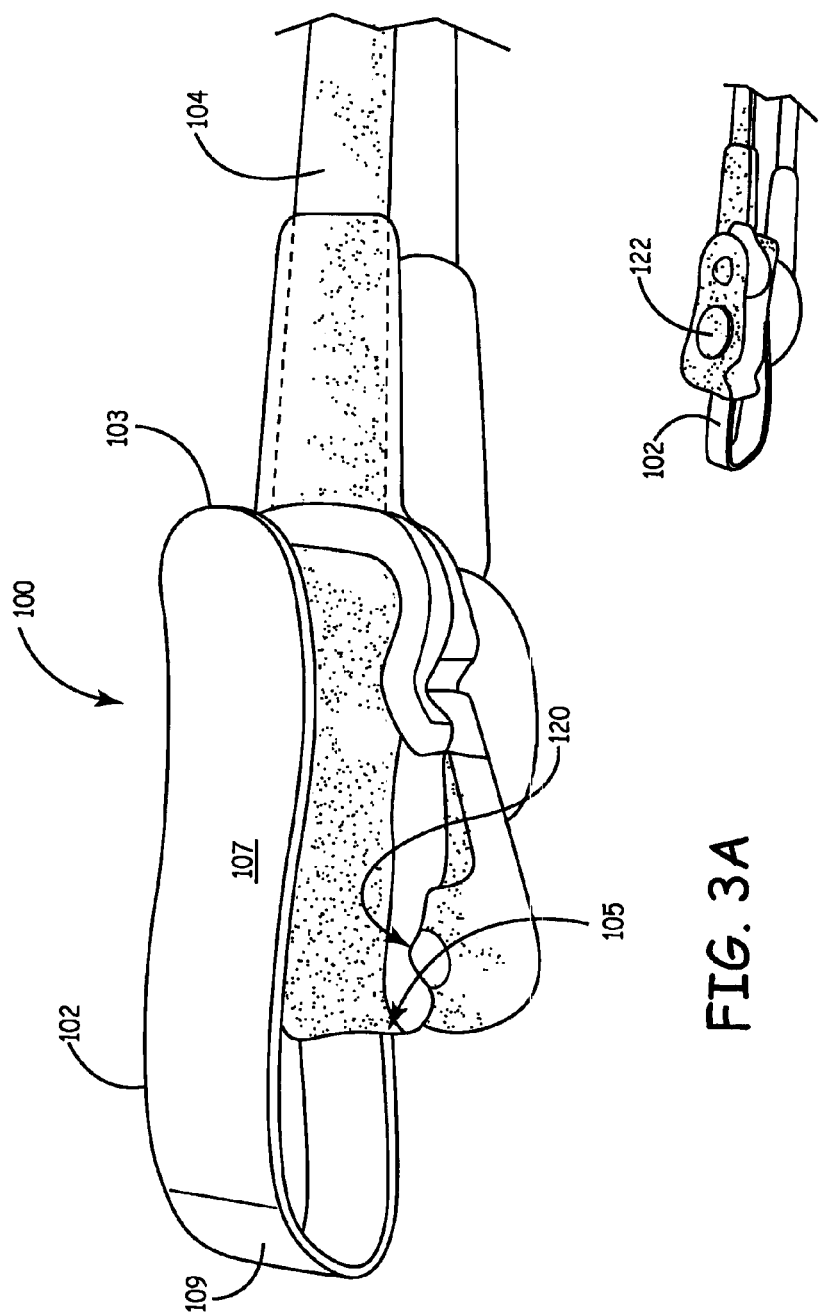

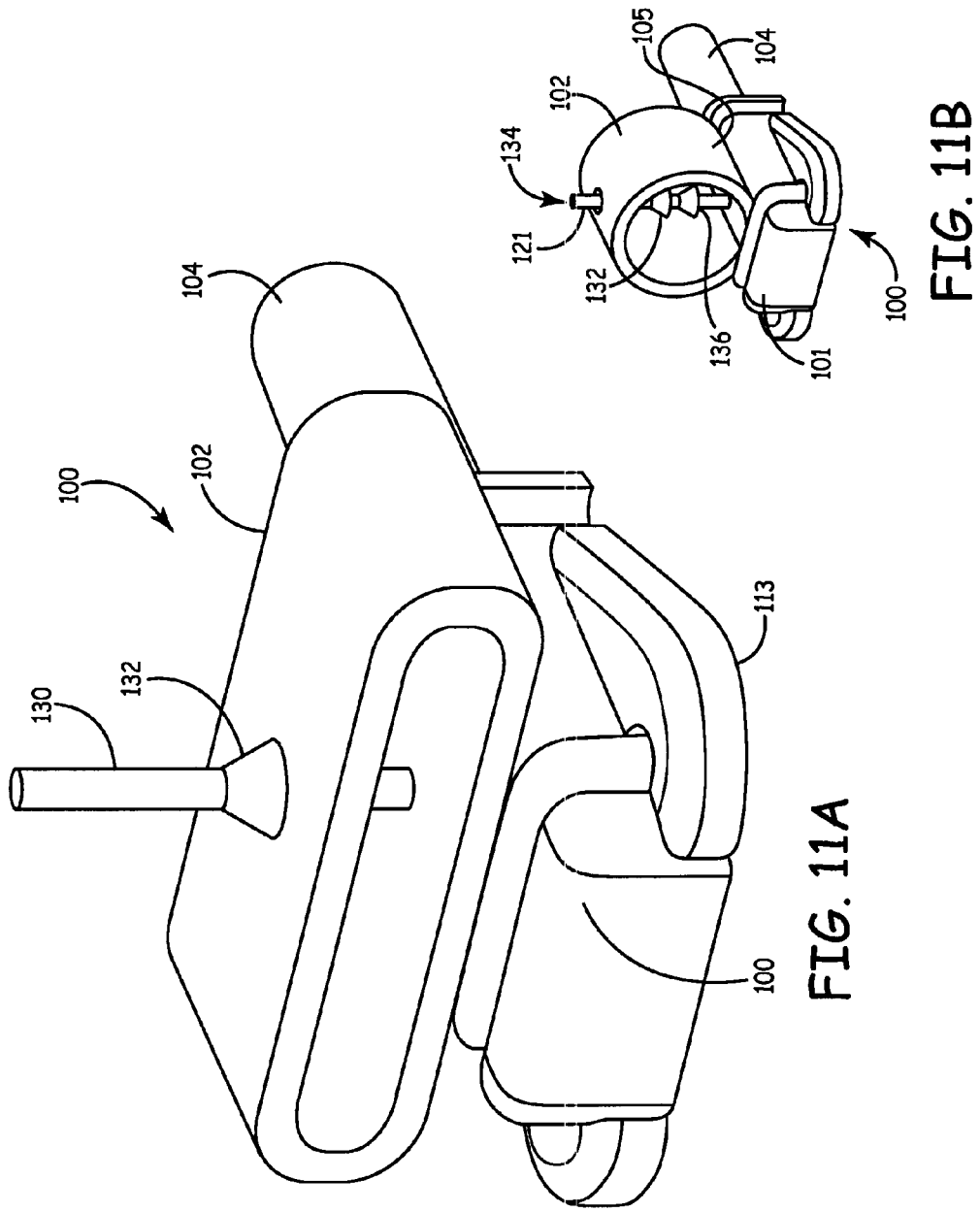

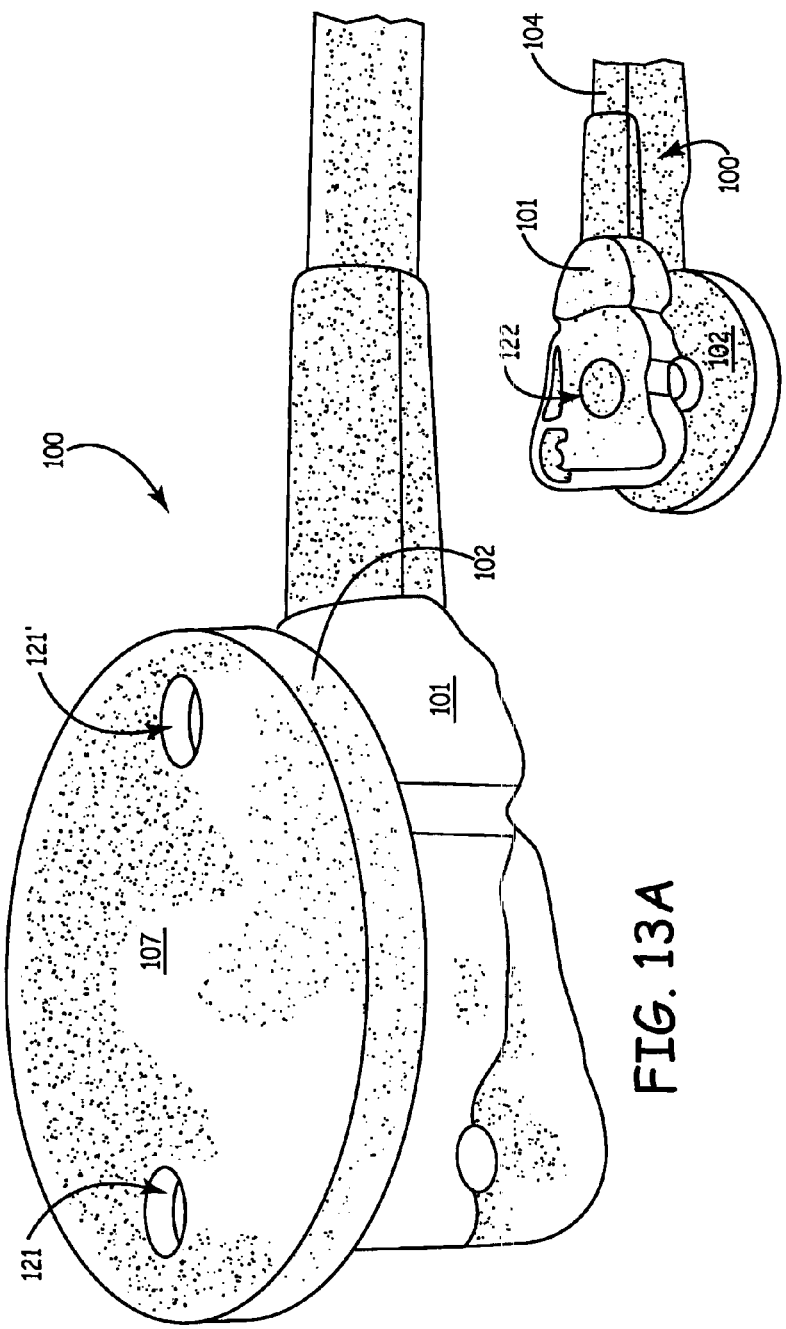

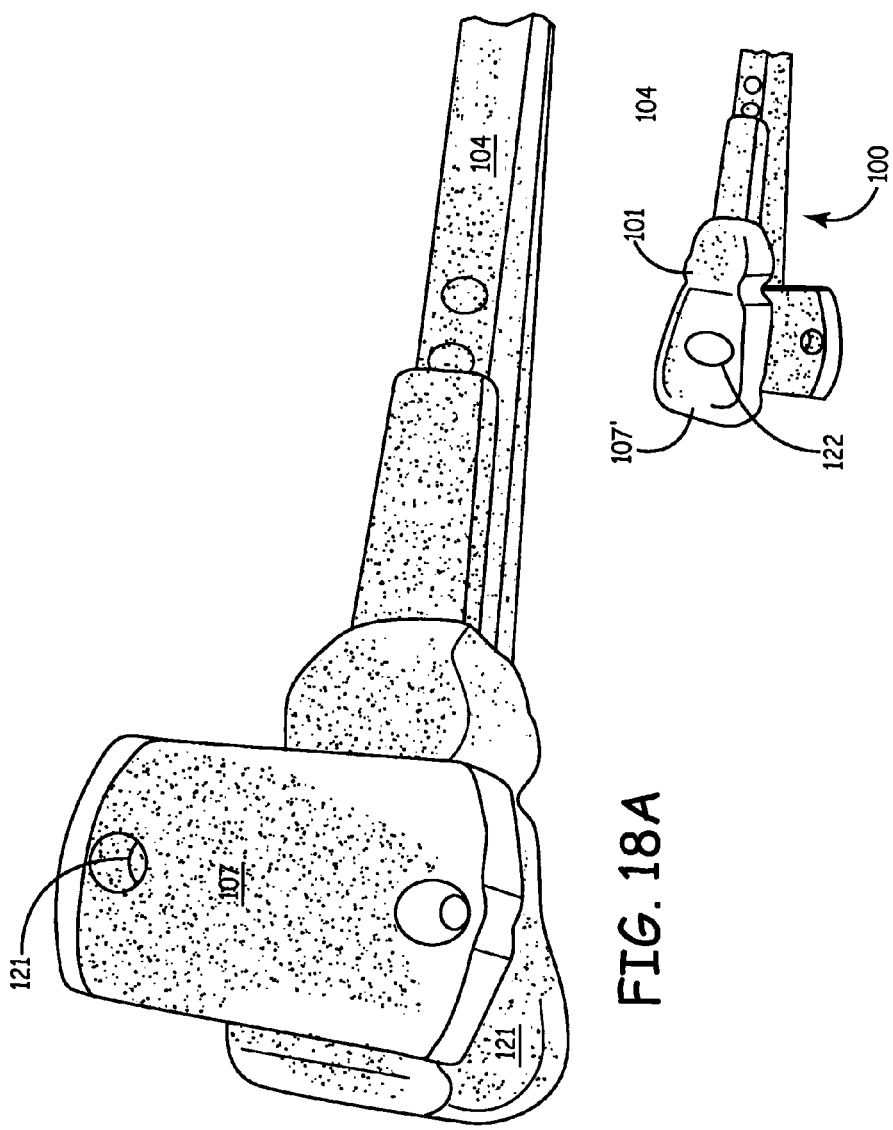

PERICARDIUM FIXATION CONCEPTS OF EPICARDIUM PACING LEADS AND TOOLS

CROSS REFERENCE TO RELATED APPLICATIONS AND PATENT

The present disclosure relates to the following co-pending applications; namely, U.S. application Ser. No. 11/000,539 by Morris et al. entitled, "METHODS AND SYSTEMS FOR ACCESSING THE PERICARDIAL SPACE" and U.S. application Ser. No. 11/000,538 by Sigg et al. captioned, "Methods and Systems for Providing Therapies into the Pericardial Space," and U.S. application Ser. No. 11/380,228 entitled, "APPARATUS AND METHODS FOR VACUUM-AND MECHANICALLY-ASSISTED FIXATION OF MEDICAL ELECTRICAL LEADS," filed on common day herewith, the contents of which are incorporated herein by reference. In addition, this disclosure incorporates the contents of U.S. Pat. No. 6,613,062 to Leckrone et al. captioned, "METHOD AND APPARATUS FOR PROVIDING INTRA-PERICARDIAL ACCESS," which issued 2 Sep. 2003.

BACKGROUND

Certain embodiments in the present disclosure pertain to medical component delivery and more particularly to tools for delivering active medical components for chronic attachment within the pericardial space.

In certain instances, a patient suffering from bradycardia, tachyarrhythmia and/or heart failure will benefit from electrical stimulation pacing and/or defibrillation electrodes implanted on an epicardial surface of the patient's heart. Minimally invasive methods for accessing the epicardial surface, which is enclosed within a pericardial sac, have recently been developed; these methods provide for piercing through the pericardial sac in order to access the epicardial surface; an example of one such method is described in commonly assigned U.S. Pat. No. 6,837,848. These methods may be used by way of a mini-thoracotomy or in conjunction with a trocar, canula or catheter that has been passed, via a percutaneous incision, through an interstitial space between the patient's ribs, via a supramanubrial or a sub-xiphoid approach or with a jugular-type access; those skilled in the art are familiar with these techniques.

Once access to the epicardial surface is established, the implanting physician may desire to implant into the pericardial space a medical electrical lead, including an appropriate electrode configuration and/or one or more physiologic sensors suited to the patient's need. The physician will almost always need to maneuver the electrode-bearing portion of the lead within the space in order to implant the components at an appropriate location and in a way to provide effective and stable chronic cardiac therapy and/or monitoring of various physiologic parameters.

SUMMARY

Certain embodiments of the present invention pertain to methods and apparatus for providing positive fixation of medical components to a portion of incised pericardial tissue. According to the diverse embodiments of the present invention, a resilient member protrudes through an incision in the pericardium and produces a positive biasing force to adjacent pericardial tissue against a side surface of a body structure. In some embodiments the resilient member can be temporarily compressed during implantation and then relaxed to thereafter provide the positive biasing force.

Diverse medical components can thus be safely and reliably chronically deployed into the pericardial space, including without limitation, cardiac sensing/pacing, defibrillation and/or cardioversion electrodes, mechanical and/or metabolic sensors and the like. In addition, one or more surface portions or apertures formed in the body or the resilient member can be coated or filled with biologic, genetic and/or pharmacologic substances. A related aspect also involves a coating of slow-release molecules or substances (e.g., steroid eluting material coated over a portion of an electrode surface). More than one body structure can be linked to a single medical electrical lead and the medical components can couple within and/or upon a portion of the body structure, the resilient member, and the lead in myriad configurations.

It should be noted that, although most embodiments of the present invention are described herein in the context of epicardial sensing/pacing, cardioversion and/or defibrillation and diverse physiologic sensing applications, the invention is not so limited. Those skilled in the art will appreciate that numerous minor alterations and modifications can be implemented to provide a wide variety of cardiac therapies, diagnostics and/or monitoring capabilities. For example, while not specifically depicted herein the present invention can be used to deliver so-called paired-and coupled-pacing therapy whereby a pacing stimulus delivered immediately following the end of the refractory period causes an extra-systole for subsequent cardiac cycles. Also, so-called non-excitatory stimulation can be delivered in which electrical stimulation is delivered during the refractory period (absolute and/or relative) to provide contractility benefits and the like.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

FIGS. 1A and 1B are a perspective view and a side elevational view, respectively, depicting certain aspects of one form an active pericardial fixation apparatus according to the invention.

FIGS. 2A and 2B are a perspective view and a side elevational view, respectively, depicting certain aspects of one form an active pericardial fixation apparatus according to the invention.

FIGS. 3A and 3B are a perspective view and a side elevational view, respectively, depicting certain aspects of one form an active pericardial fixation apparatus according to the invention.

FIGS. 11A and 11B are perspective views depicting certain aspects of one form an active pericardial fixation apparatus according to the invention wherein said apparatus is shown in a compressed state and a relaxed state.

FIGS. 13A and 13B are perspective photographic views depicting a method of progressively deploying the active pericardial fixation apparatus according to an embodiment of the invention depicted in FIG. 12.

FIGS. 18A-18B are perspective photographic views depicting a related form of the active pericardial fixation apparatus according to the embodiment of the invention depicted in FIGS. 16A, 16B, and 17.

DETAILED DESCRIPTION

Figure 4:
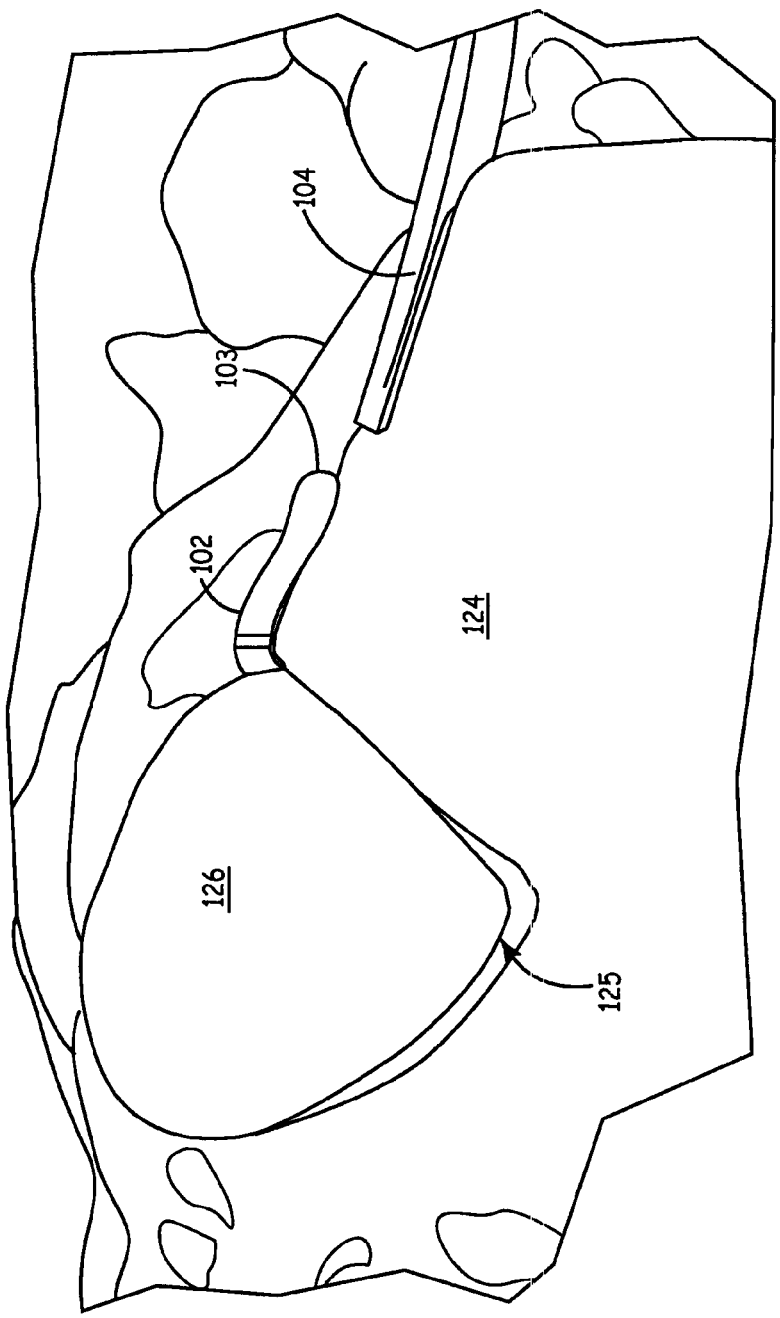
FIG. 4 is a photographic depiction of an embodiment of the invention as depicted in FIGS. 2A-B and 3A-B fixedly engaging an edge of an incision through the pericardium of a heart.

The following detailed description is exemplary in nature and is not intended to limit the scope, applicability, or configuration of the invention in any way. Rather, the following description provides practical illustrations for implementing exemplary embodiments of the present invention.

As is known to those in the art of cardiac surgery, electrophysiology, and/or interventional cardiology, an exemplary delivery tool is used to position a medical electrode assembly and/or a physiologic sensor which couples to a portion of a medical electrical lead for deployment of the assembly and/or sensor to an epicardial surface of a heart. According to some embodiments of the present invention, the assembly and/or sensor include one or more pacing or defibrillation electrodes and a physiologic sensor (e.g., a metabolic sensor, a mechanical sensor such as an accelerometer or the like, a pressure sensor, etc.). In addition, more than one electrode and/or sensor assembly can be deployed on a single medical electrical lead or dedicated electrode units and dedicated sensor units can be deployed individually or coupled to a common lead or several dedicated medical electrical leads. Known electrical multiplexing techniques can be used to provide and receive signals from the units.

A proximal end of a medical electrical lead operatively couples the unit or units to pacing, sensing, and/or cardioversion/defibrillation circuitry, in the case of electrodes, and to appropriate signal processing circuitry, in the event that sensors are deployed.

A variety of deployment techniques and delivery tools can be used in conjunction with the apparatus of the present invention that would typically include an elongated shaft having a distal portion coupled to a shaft portion. During deployment the distal portion is inserted between an epicardial surface of the heart and a pericardial sac surrounding the heart through a pericardial incision. According to certain embodiments of the present invention, the shape of the distal portion can be adjusted to facilitate insertion of the assembly and/or sensor between the pericardium and epicardium.

FIGS. 1A and 1B are a perspective view and a side elevational view, respectively, depicting certain aspects of one form an active pericardial fixation apparatus 100 according to the invention. As shown in FIG. 1A a body structure 101 couples to a portion of an elongated medical electrical lead 104, which as depicted is shown coupled (at side portion 108) to a distal end portion of the lead 104 although the body structure could couple to an intermediate portion of the lead 104 and/or the lead 104 can couple to other side portions (106, 112, 116) or the upper portion (114) of the body structure 101. The embodiment of the apparatus 100 depicted in FIG. 1A includes optional lateral support members 113 coupled to side portion 112. Although not depicted in FIG. 1A, one or more electrode and/or sensor units operatively couple to a remote medical device via lead 104 from a location on a surface of body structure 101. For example, the apparatus 100 can include one or more electrodes coupled to the major lower surface of the body structure 101 in electrical communication with a portion of epicardial tissue while one or more physiologic sensor units reside within or on another part of the body structure 101, a part of an active fixation member 102, and/or a portion of the lead 104. The active mechanical fixation member 102 is adapted to engage at least an edge portion of an incision in the pericardial sac couples to a portion of the body structure 101. As depicted, the fixation member 102 couples at 105 to side wall 106 and extends through a curved portion 109 toward an end 103.

As shown in FIG. 1B, the fixation member 102 is configured with a major radius portion between curved portion 109 and end 103 so that a region of reduced spacing is provided between the member 102 and the side portion 114. When deployed a portion of pericardial tissue is retained in this region. As noted above, although depicted as coupled to side portion 106, the fixation member 102 could couple to side portion 112 (or 114, 116). The fixation member 102 can comprise a hollow member, a solid member or a porous or perforated member of varying dimension (e.g., length, width, shape, etc.) composed of a resilient biocompatible material. For example, according to some embodiments of the invention body structure 101 and/or fixation member 102 can be comprised of a biocompatible polymer. The structure 101 and member 102 can be injection molded from a polymer having a relatively high modulus of elasticity, yet being sufficiently elastic and not prone to brittle fracture, for example 75 D durometer polyurethane or high density polyethylene or polyamide. Alternately, one or both can be insert molded or formed by molding or an extrusion process. According to some embodiments, fixation member 102 can be wholly or partially formed from a metal having suitable elastic and elastomeric properties, examples of which include, but are not limited to, titanium alloys, Ni—Ti super-elastic alloys and stainless steel and the like. Other suitable materials can also be used as known in the art.

FIGS. 2A and 2B are a perspective view and a side elevational view, respectively, depicting certain aspects of one form an active pericardial fixation apparatus 100 according to the invention. While other differences can be implemented or appreciated with respect to the apparatus 100 herein depicted versus the apparatus 100 of FIG. 1A, primarily the fixation member 102 has been modified so that in lieu of a tubular member a member having a major surface 107 and the end 103 has a relatively straight portion. Of course, the end 103 can be contoured or curved without sacrificing the utility of the member 102. Furthermore, as depicted the end 103 includes an enlarged and rounded portion which can optionally be utilized to increase the possibility of smooth insertion and retention of a portion of the pericardial sac.

FIGS. 3A and 3B are a perspective view and a side elevational view, respectively, depicting certain aspects of the form of an active pericardial fixation apparatus according to the invention substantially as depicted in FIG. 2A. As shown the major surface 107 terminates at end 103 with a gradually curving edge devoid of the enlarged and rounded portion depicted in FIG. 2A although such a feature can of course be incorporated into the apparatus depicted in FIG. 3A.

FIG. 4 is a photographic depiction of an embodiment of the invention substantially as depicted in FIGS. 2A-B and 3A-B with the member 102 having a rounded end portion 103 fixedly engaging an edge of an incision 125 through the pericardial sac 124 of a heart and includes an exposed portion of epicardial tissue 126. Lead 104 includes elongated conductors to transfer power and/or signals to and from electrodes and/or sensor units disposed in, on, or about the apparatus 100 and/or lead 104 to operative electronic circuitry (not depicted).

Figure 5A:
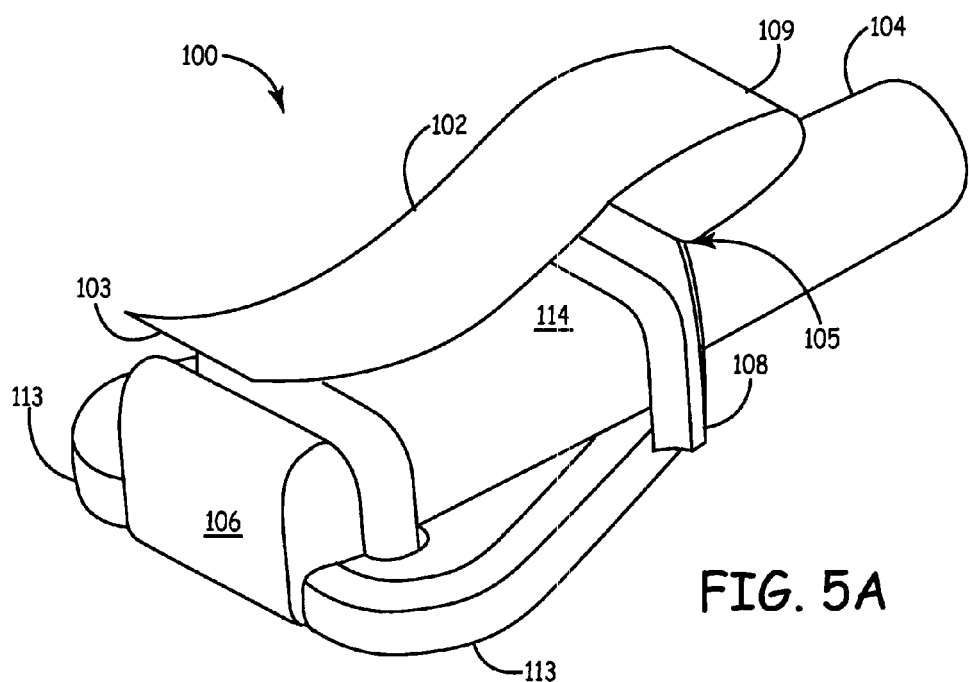
FIGS. 5A and 5B are a perspective view and a side elevational view, respectively, depicting certain aspects of one form an active pericardial fixation apparatus according to the invention.
Figure 5B:
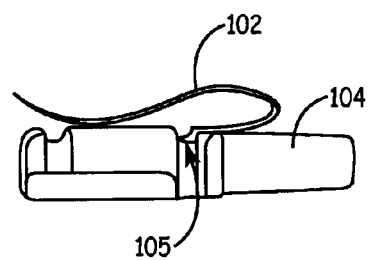

FIGS. 5A and 5B are a perspective view and a side elevational view, respectively, depicting certain aspects of another form of an active pericardial fixation apparatus 100 according to the invention. Inspection of FIGS. 5A and 5B reveals that the fixation member 102 couples at 105 to side portion 108. Thus, the curved portion 109 is disposed near the lead 104. During deployment this embodiment can be advanced into retaining engagement with a portion of pericardial tissue whereas the previously-discussed embodiments were initially advanced and then reversed to engage the pericardial tissue. The lateral members 113 can be configured to improve ease of deployment and electrode communication or contact with the epicardial tissue (e.g., sloped or enlarged or the like). To further promote such communication or contact an electrode can be disposed between lateral members 113 and directly aligned with the most narrow spacing between surface 114 and the fixation member 102. As depicted the end 103 extends slightly beyond the side portion 106 although this is not a requirement of this embodiment of the invention (e.g., the end could terminate before or at the plane defined by side portion 106).

Figure 6:
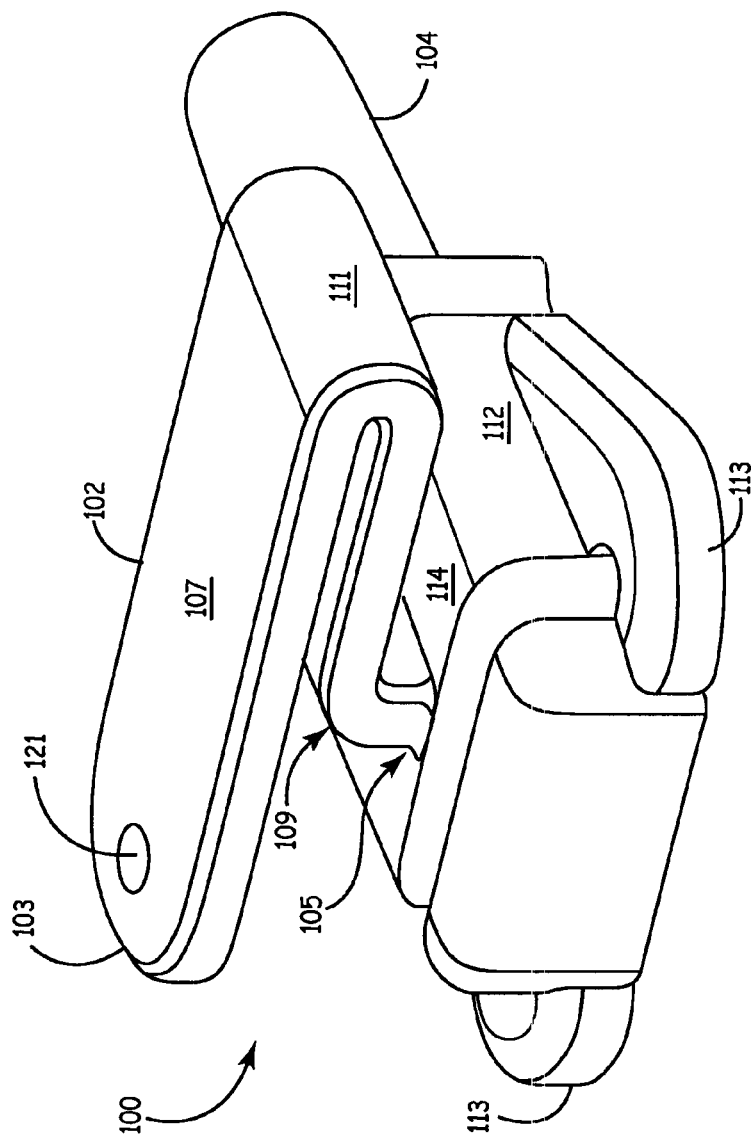
FIG. 6 is a perspective view depicting certain aspects of one form an active pericardial fixation apparatus according to the invention.

FIG. 6 is a perspective view depicting certain aspects of another form an active pericardial fixation apparatus 100 according to the invention. In this embodiment, as before, an active fixation member 102 couples to a side wall portion (in this case 114) at 105 and includes an initial curved portion 109 and extends toward an end 103. A second curved portion 111 is intermediate portion 109 and end 103 and a major surface 107 lies therebetween. Although this embodiment is depicted as including a substantially planar member a thin hollow or solid member could also be configured too. In the depicted embodiment, the major surface 107 includes an optional aperture 121. The aperture 121 can be disposed elsewhere on the surface 107 or additional apertures can be added, as desired for a given application or clinician preference. The aperture 121 is adapted to receive a tool during manual manipulation at initial implant. Subsequently the aperture 121 can be used to receive sutures to further secure the apparatus 100 in a desired location.

Figure 7A:
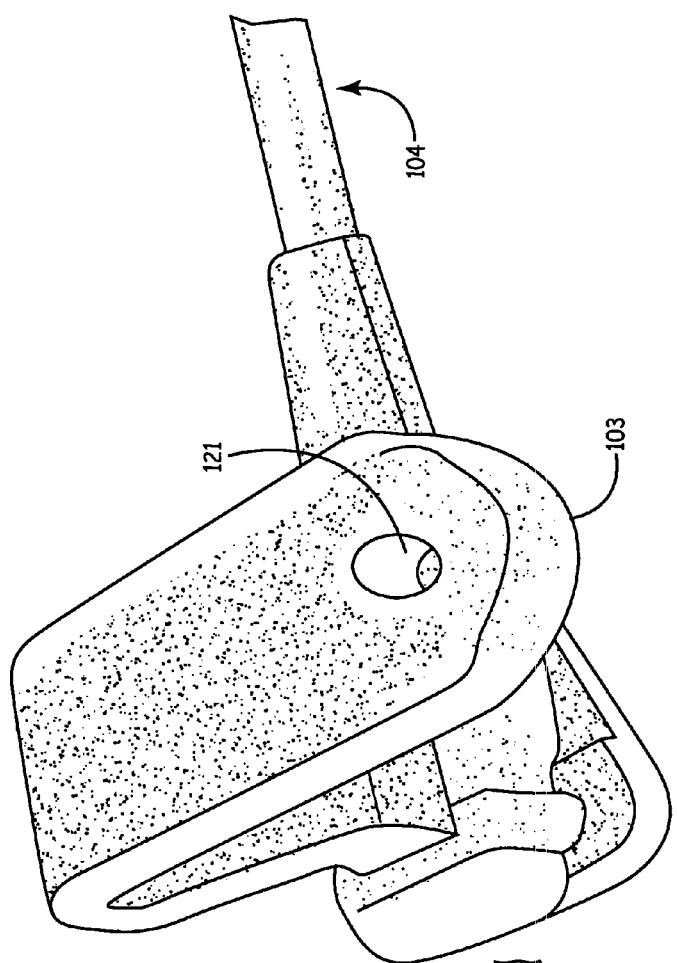
FIGS. 7A and 7B are perspective photographic views depicting certain aspects of one form an active pericardial fixation apparatus according to the invention.
Figure 7B:
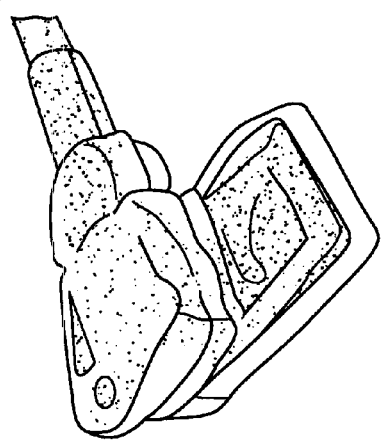

FIGS. 7A and 7B are perspective photographic views depicting certain aspects of the form an active pericardial fixation apparatus 100 according to the invention as depicted in FIG. 6 in both a relaxed and a compressed orientation, respectively.

Figure 8:
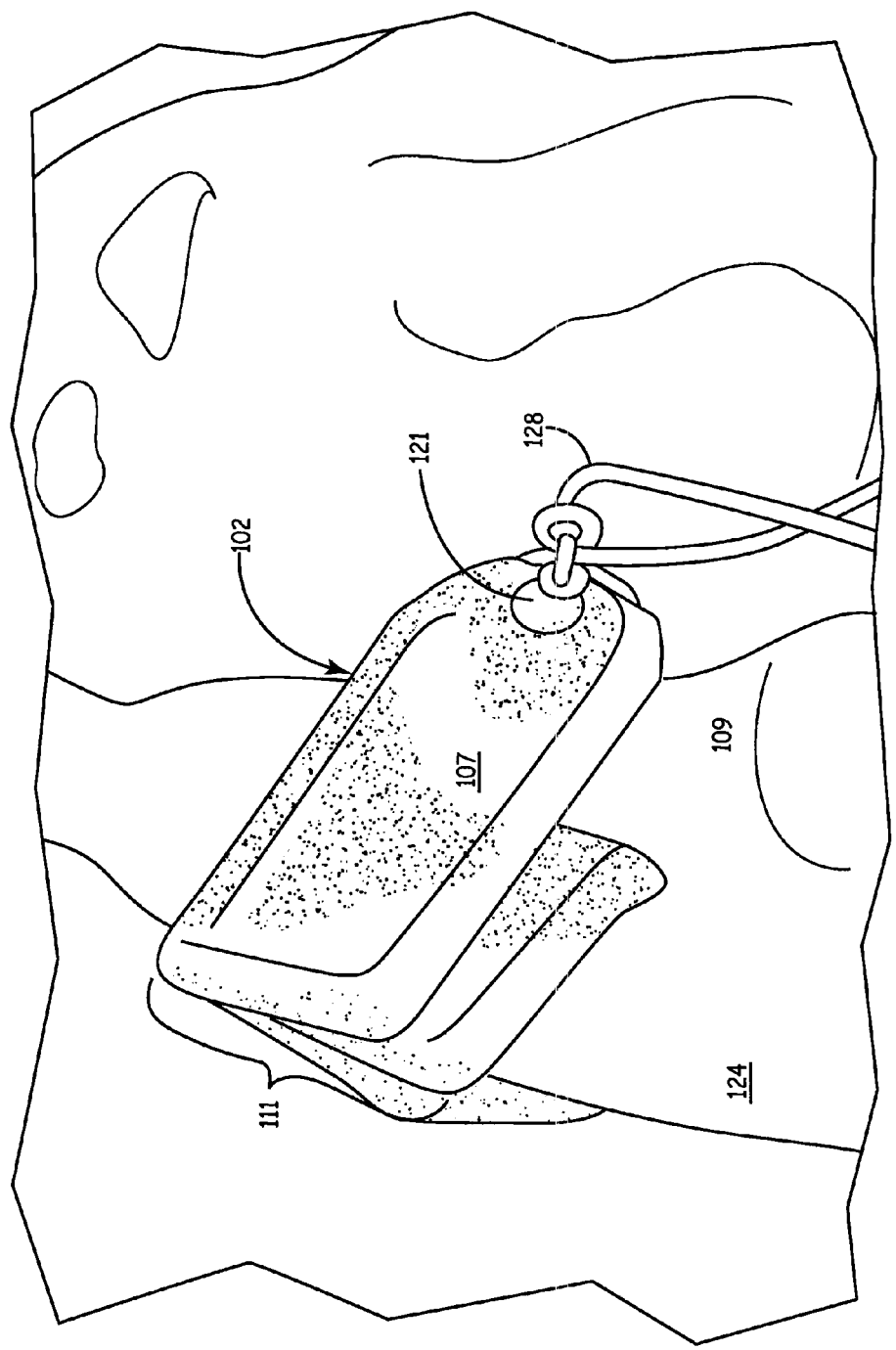
FIG. 8 a perspective photographic views depicting certain aspects of one form an active pericardial fixation apparatus according to the invention fixedly engaging an edge of an incision through the pericardium of a heart.

FIG. 8 a perspective photographic views depicting certain aspects of one form an active pericardial fixation apparatus 100 according to the invention fixedly engaging an edge of an incision through a portion of the pericardium 124 of a heart. As shown, the aperture 121 receives an elongated member, for instance surgical thread 128. In FIG. 8 the member 102 engages the pericardium 124 the pericardium is lodged at curved portion 109 in lieu of portion 111. Of course, the pericardium could be lodged at portion 111 for chronic implantation.

Figure 9:
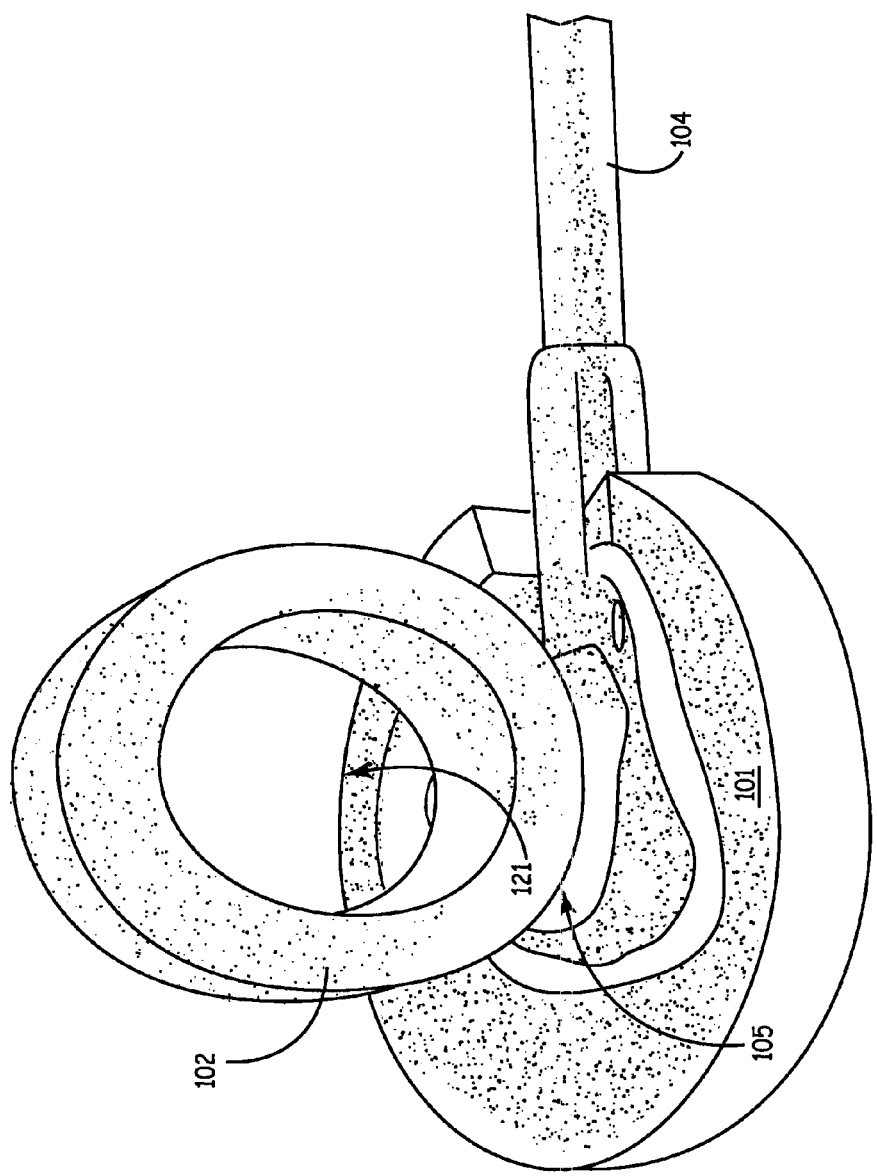
FIG. 9 is a perspective photographic view depicting a method of progressively deploying an active pericardial fixation apparatus according to an embodiment of the invention.
Figure 10A:
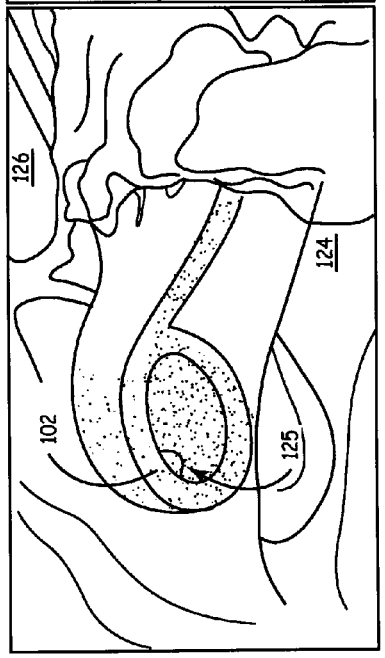
FIG. 10 is a perspective photographic view of the embodiment depicted in FIGS. 9A-9D.
Figure 10B:
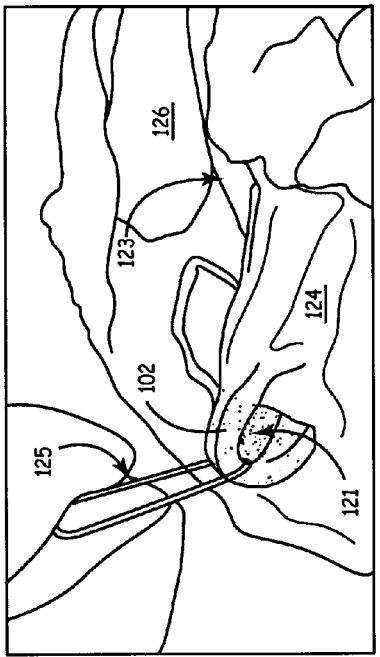
Figure 10C:
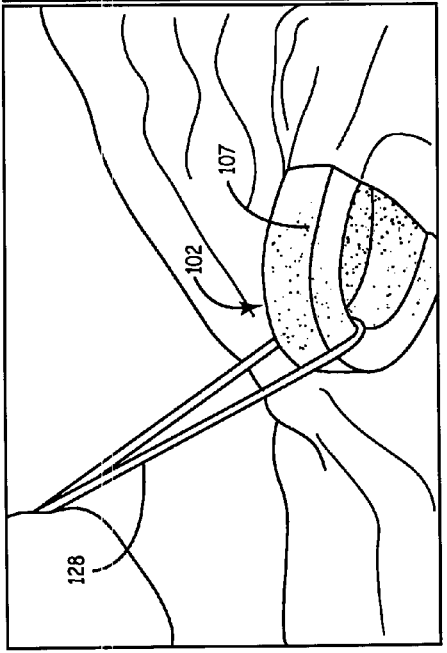
Figure 10D:
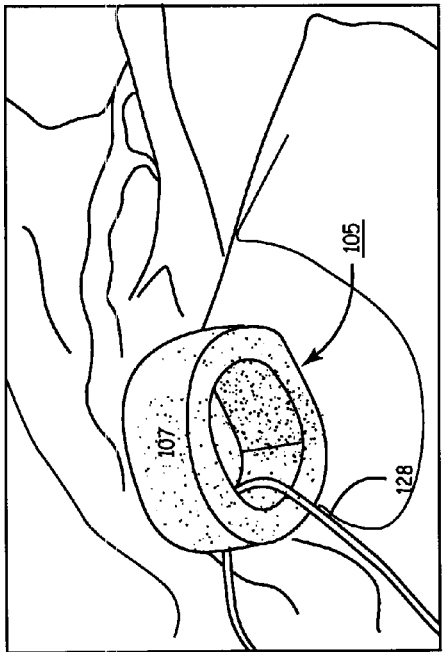

FIG. 9 is a perspective photographic view of the embodiment of the active pericardial fixation apparatus 100 depicted in FIGS. 10A-10D. In this embodiment the fixation member 102 is configured into a ring coupled at 105 to the body member 101. The ring essentially defines an optional aperture 121 that can be used to receive a tool for manually advancing the apparatus 100 through an incision in through the pericardium. Thus, as with other embodiments the body structure 101 remains fixated within the pericardial space and the fixation member 102 remains fixated to at least a portion of the pericardium surrounding the incision. FIGS. 10A-10D are perspective photographic views depicting a method of progressively deploying an active pericardial fixation apparatus 100 according to an embodiment of the invention as depicted in FIG. 9. In one form of this aspect of the invention a incision is made through first and second portions of pericardial tissue and the apparatus 100 is advanced through the first portion of pericardial tissue 123 into the pericardial space and fixated to a second portion of pericardial tissue 125 so that the curvilinear active fixation member 102 provides a mechanically-biasing force retaining the apparatus 100 in place intermediate the epicardium 126 and the pericardium 124. As shown in FIGS. 10B-D once a portion of the member 102 emerges from the second portion 125 a length of cord or other appropriate material can be optionally inserted through the member 102 which, as noted with reference to FIG. 9, comprises the ring formed by the curvilinear member 102 (although it could comprise an aperture, such as aperture 121 formed in the surface 107 as depicted in FIG. 6 and FIG. 8, as previously described).

FIGS. 11A and 11B are perspective views depicting certain aspects of one form an active pericardial fixation apparatus 100 according to the invention wherein said apparatus is shown in a compressed state (FIG. 11A) and a relaxed state (FIG. 11B). Turning first to FIG. 11B wherein the fixation member 102 comprises a ring configuration coupled to body structure 101 at 105, an elongated post 130 having a distal end 134 aligns with aperture 121. The post has at least one mechanical interlock (132,136) disposed on an intermediate portion of post 130 and sized to engage aperture 121 when the fixation member 102 is compressed. With reference to FIG. 11A, one can appreciate that the mechanical interlock 132 retains fixation member 102 in a compressed state so that pericardial tissue intermediate member 102 and body structure 100 is fixated therebetween. Deployment of this embodiment of the apparatus 100 can be implemented similar to that described with reference to FIGS. 10A-D with the additional step of compressing the member 102 until aperture 121 engages mechanical interlock 132 (or optionally interlock 136). The interlock feature can comprise a wide variety of shapes and sized (e.g., an enlarged portion, a rib member, a frustoconical portion, a boss, a protuberance, a ring feature, an interlocking flange, a shelf, protruding edge, a collar, etc.).

Figure 12:
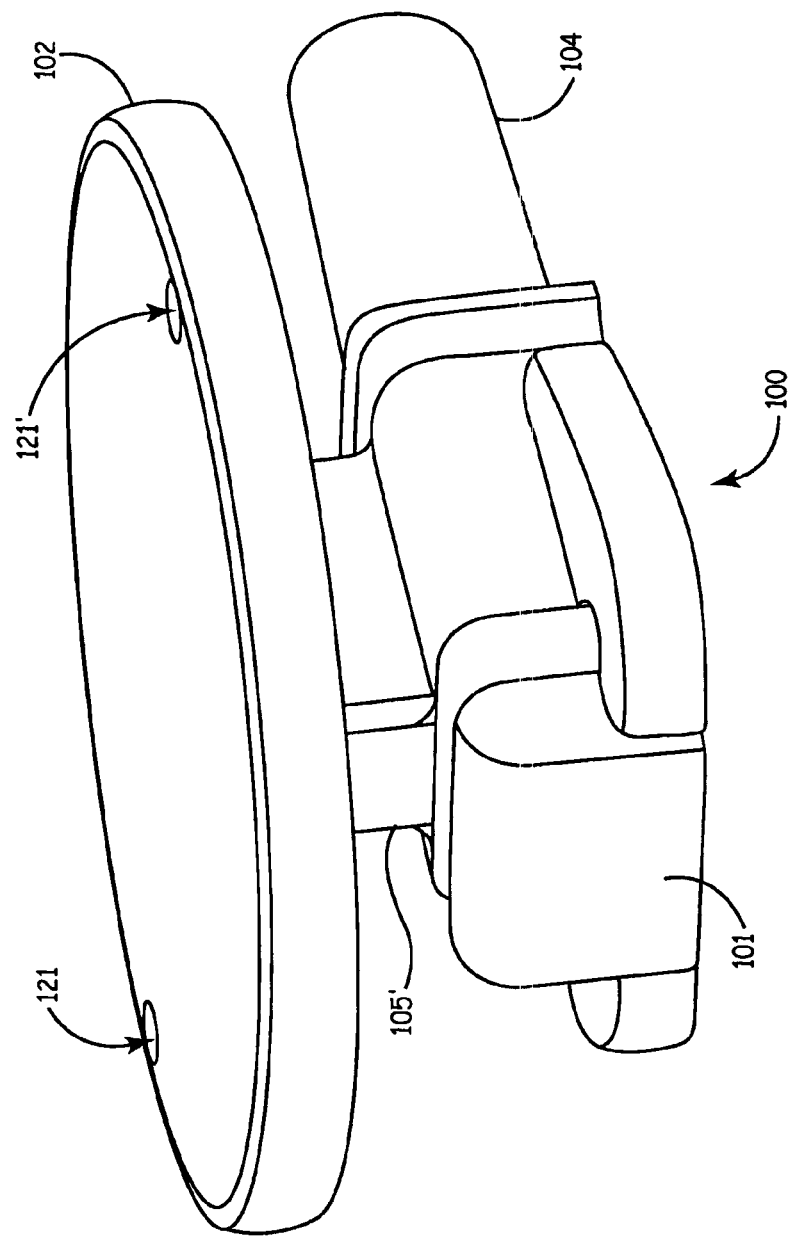
FIG. 12 is a perspective view depicting yet another embodiment of the present invention.

FIG. 12 is a perspective view depicting yet another embodiment of the pericardial fixation apparatus 100 of the present invention. In this embodiment the body structure 101 couples to an extended coupling location 105 for the fixation member 102. Member 102 is depicted in a relaxed state, but the member 102 includes two spaced apart apertures 121,121' which can receive a tool (not shown) thus binding the apertures together and rending the member 102 into a compressed state while also providing convenient access to manually pull the apparatus 100 through a pericardial incision. Thus, while in the compressed state the member 102 more readily advances through an incision in the pericardium or can be advanced through a relatively smaller incision as will be described with reference to FIGS. 14A-D herein.

FIGS. 13A and 13B are perspective photographic views depicting a method of progressively deploying the active pericardial fixation apparatus 100 according to an embodiment of the invention depicted in FIG. 12. In FIG. 13A the major surface 107 of member 102 is shown which includes two apertures 121,121'. In FIG. 13B, the epicardial-contacting side of the body 101 is shown and the location 122 for receiving an electrode and/or other sensor unit or component. Note that in the case one or more physiologic sensing units are included with the apparatus 100 said units can couple within and/or on the body structure 100, the fixation member 102 and/or the lead 104. The electrode(s) can comprise one or more pacing/sensing (mono-or multi-polar), defibrillation, and/or cardioversion electrodes such electrodes can be used to register temporal traces of cardiac activity and/or to register impedance measurements on diverse vectors between extant electrodes (including housing-or can-based electrodes, endocardial electrodes, other epicardial electrodes, etc.). The sensing unit(s) can comprise one or more metabolic sensors, such as optical-type oxygen sensor, a lactate sensor, a glucose sensor, a potassium sensor, a calcium sensor, a thrombin sensor, a carbon dioxide sensor, etc. and/or mechanical sensors, for example single-or multi-axis accelerometers, pressure sensors, and the like.

Figure 14A:
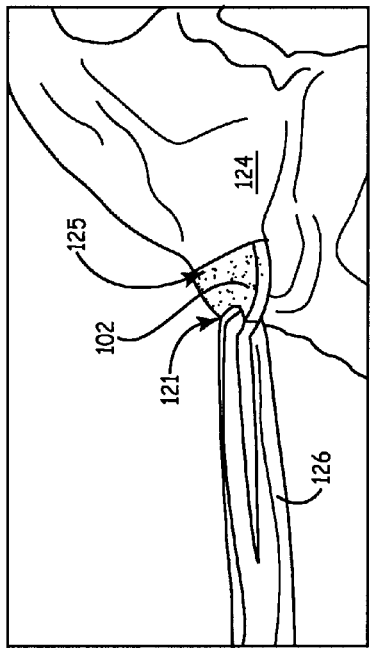
FIGS. 14A-14D are perspective photographic views depicting a method of progressively deploying an active pericardial fixation apparatus according to the embodiment of the invention depicted in FIGS. 12, 13A, and 13B.
Figure 14B:
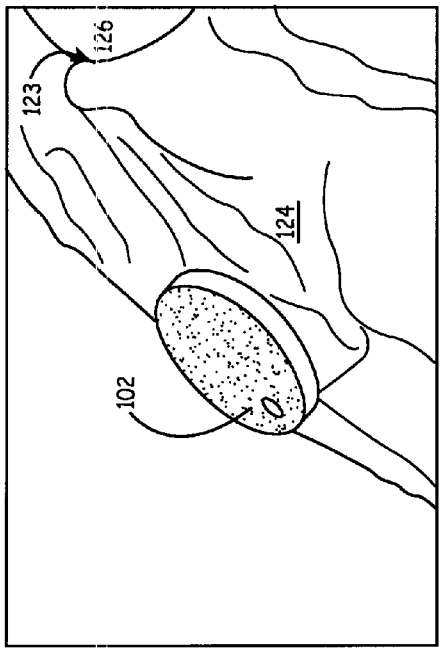
Figure 14C:
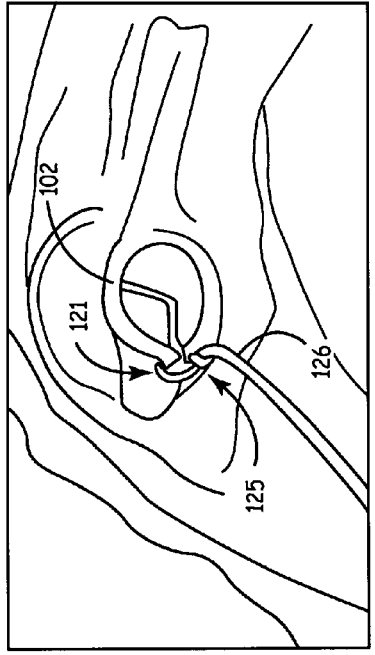
Figure 14D:
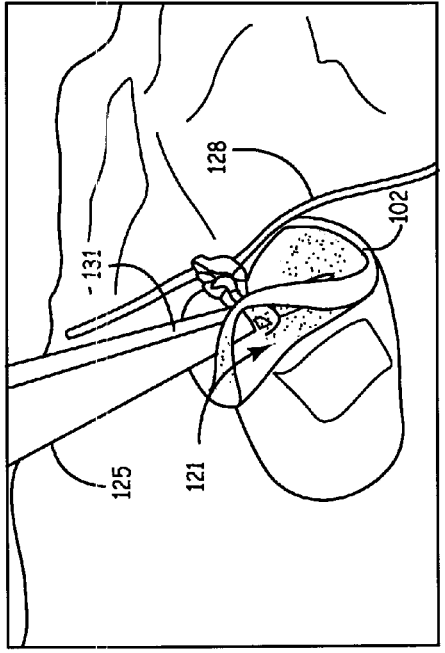

FIGS. 14A-14D are perspective photographic views depicting a method of progressively deploying an active pericardial fixation apparatus 100 according to the embodiment of the invention depicted in FIGS. 12, 13A, and 13B. In FIG. 14A, the apparatus 100 can be seen emerging from an incision 125 in the pericardium in the compressed state. The compressed state is achieved with an elongated segment of cord 128 binding apertures 121,121' together so that member 102 more readily can be drawn through the incision 125. Alternatively, as depicted in FIG. 14B an elongated tool 126, such as a forceps, can be used to engage one or both of the apertures 121,121' to manually assist the emergence of the member 102 from the incision 125 in the pericardium 124. In FIG. 14C the member 102 is shown in the compressed state due to the cord 128 binding the apertures 121,121' and the sharp edge 131 of a sharp instrument 129, such as a scalpel, can be used to sever the cord 128 thus rendering the member 102 into the relaxed state (shown in FIG. 14D). Thus, once deployed through a first incision 123 in the pericardium 124 and allowed to return to the relaxed state the fixation member 102 provides a biasing force upon a portion of pericardium disposed between the body structure 101 and the member 102. Optionally, the first incision 123 and/or second incision 125 can be sutured (closed) thereby further fixating the apparatus 100 and allowing chronic cardiac rhythm management monitoring, therapy delivery and/or diagnostics to be implemented.

Figure 15:
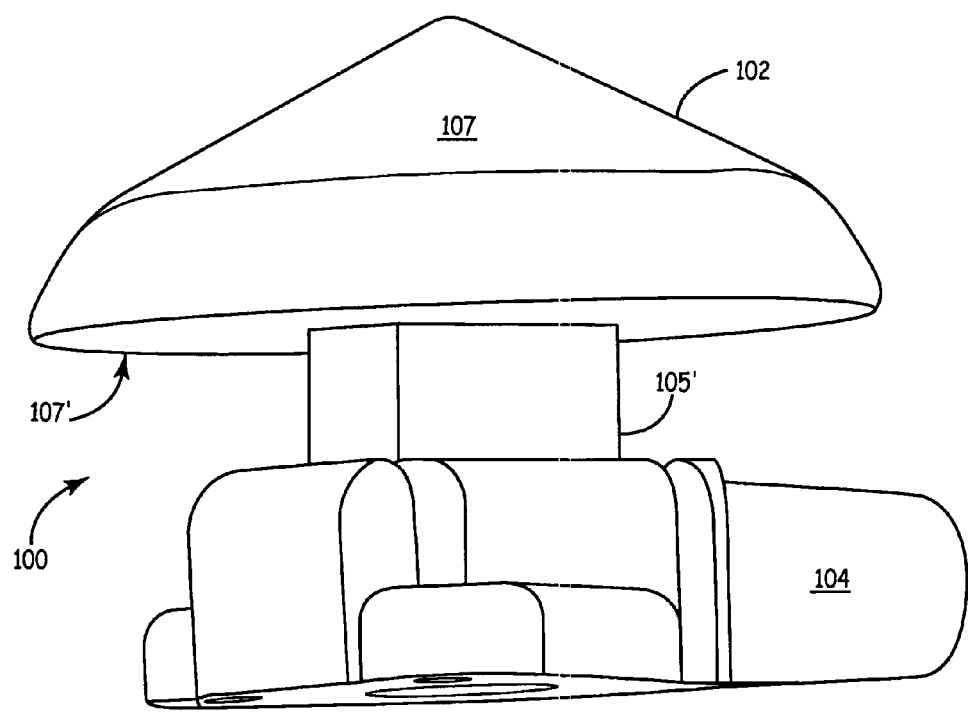
FIG. 15 is a side-elevational perspective view depicting yet another embodiment of the present invention.

FIG. 15 is a side-elevational perspective view depicting yet another embodiment of a pericardial fixation apparatus 100 according to the present invention. In this embodiment the major surface 107 of fixation member 102 is not substantially parallel to the opposing major surface 107' which, in this depiction, comprises a substantially planar surface. However, according to the invention one or both major surface 107,107' can include diverse surface features. Such features can comprise for example, an irregular surface, a curved surface, a curvilinear surface, a convex surface, a convex surface, a complex surface, a faceted surface, a conical surface, a perforated surface, a ribbed surface, and the like.

Figure 16A:
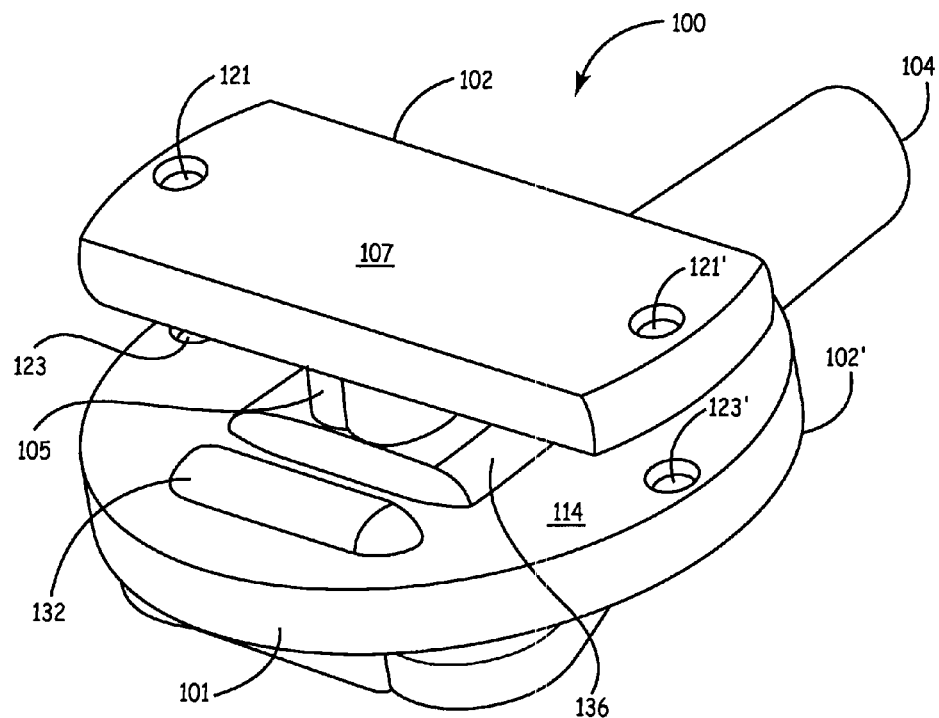
FIGS. 16A and 16B are perspective views depicting certain aspects of one form an active pericardial fixation apparatus according to the invention wherein said apparatus is shown in a compressed state and a relaxed state.
Figure 16B:
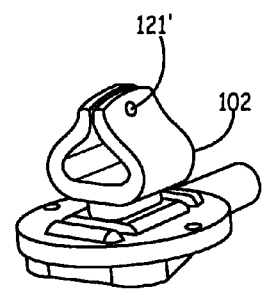

FIGS. 16A and 16B are perspective views depicting certain aspects of one form an active pericardial fixation apparatus 100 according to the invention wherein said apparatus 100 is shown in a compressed state (FIG. 16B) and a relaxed state (FIG. 16A). This embodiment is somewhat similar to embodiments depicted in FIGS. 12, 13A, 13B, and 14A-D with a couple of exceptions. For example, additional apertures 123,123' appear on laterally extending portions of body structure 101 (denoted as 102') and the fixation member 102 is configured in a rectangular configuration in lieu of a circular configuration (in plan view). Also, optional features similar to the previously depicted and described mechanical interlock members 132,136 are provided on the side surface 114 of the body structure 101. The members 132,136 are configured to provide an additional amount of fixation by impinging upon pericardial tissue intermediate the structure 101 and the fixation member 102 following implantation. In FIG. 16B the member 102 is depicted in the compressed state which can be optionally utilized during implantation substantially as previously described.

Figure 17:
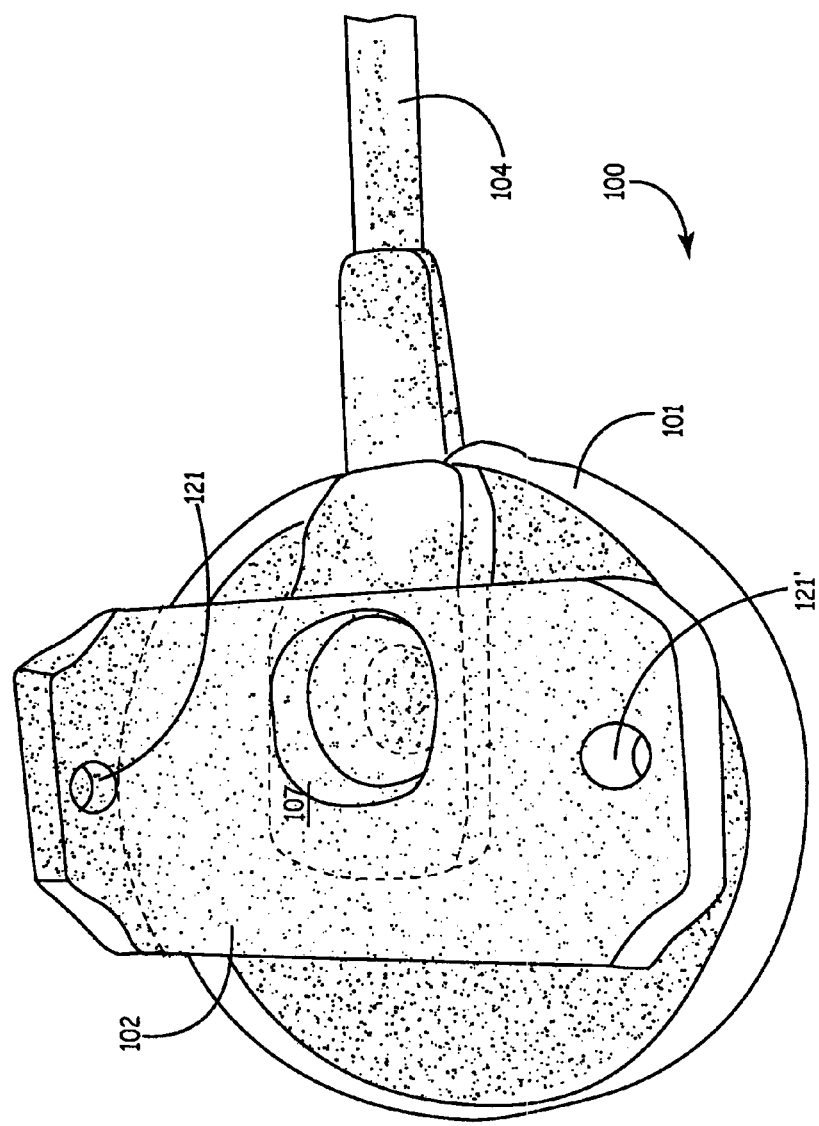
FIG. 17 is a perspective photographic view of the embodiment depicted in FIGS. 16A-16B (in a relaxed state).

FIG. 17 is a perspective photographic view of the embodiment of the apparatus 100 depicted in FIGS. 16A-16D (in a relaxed state). In this view the major surface 107 includes two apertures 121,121' and optionally includes beveled, or clipped, corner portions of the substantially rectangular member 102.

FIGS. 18A-18B are perspective photographic views depicting a related form of the active pericardial fixation apparatus 100 according to the embodiment of the invention depicted in FIGS. 16A, 16B, and 17. Although these views reveal that the member 102 includes rounded edges that define the substantially rectangular major surface 107. In FIG. 18B, a location 122 for receiving an electrode and/or sensor is depicted as residing upon opposing major surface 107' of the body 101. Of course, the electrode and/or sensor mechanically couples to the body structure 101 and electrically couples via the lead 104 to operative circuitry.

Figure 19A:
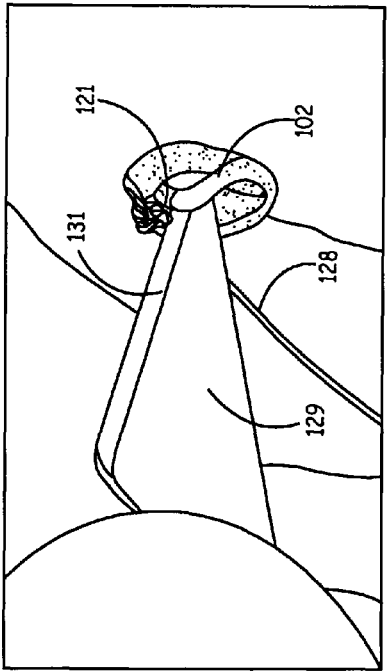
FIGS. 19A-19D are perspective photographic views depicting a method of progressively deploying an active pericardial fixation apparatus according to the embodiment of the invention depicted in FIGS. 16A, 16B, 17, 18A, and 18B.
Figure 19C:
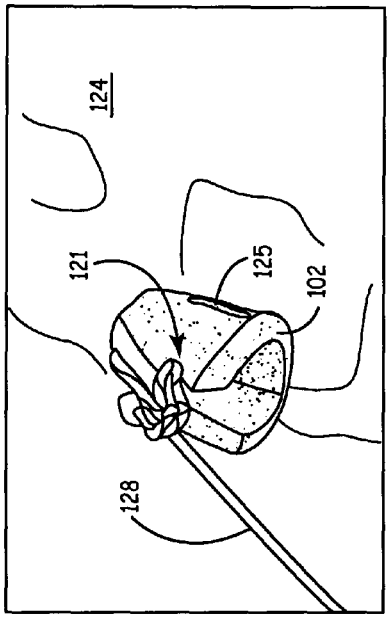
Figure 19B:
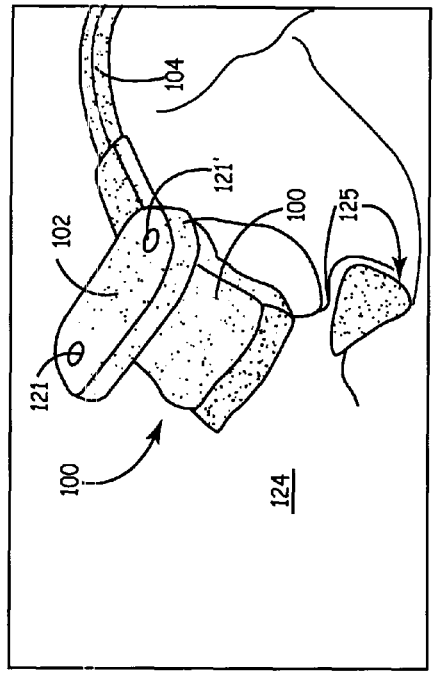
Figure 19D:
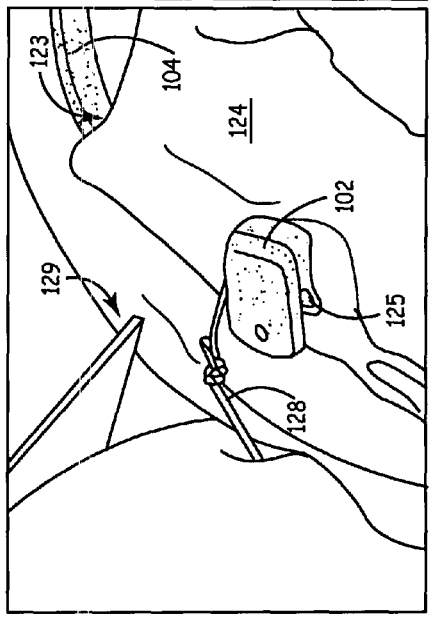

FIGS. 19A-19D are perspective photographic views depicting a method of progressively deploying an active pericardial fixation apparatus 100 according to the embodiment of the invention depicted in FIGS. 16A, 16B, 17, 18A, and 18B. In FIG. 19D, the apparatus 100 is shown in a relaxed state disposed near an incision 125 in the pericardium 124 of a heart and coupled to lead 104. This embodiment includes two apertures 121,121' which are coupled together to render the fixation member in a compressed state during implantation. Now referring to FIG. 19A, the fixation member 102 is depicted partially protruding through the incision 125 in the pericardium 124 while configured in the compressed state due to the cord 128 connected through apertures 121,121'. In FIG. 19B, the sharp edge 131 of a tool 129, such as a scalpel, is used to sever the cord 128. As seen in FIG. 19C once the cord 128 is severed and removed, the member 102 returns to a relaxed state thereby providing positive mechanical fixation to the portion of pericardium 124 adjacent incision 125 disposed between the body 101 and the member 102.

Figure 20A:
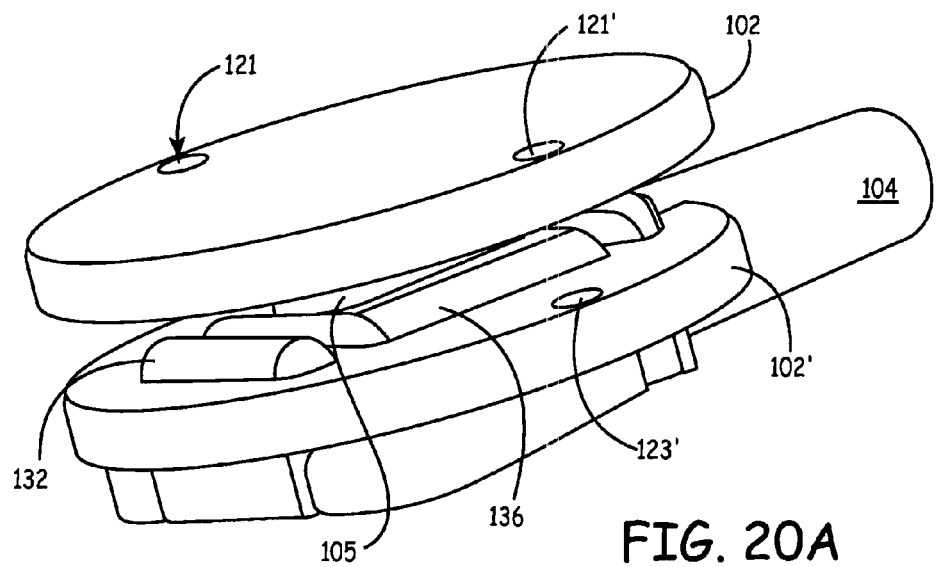
FIGS. 20A, 20B, and 20C are perspective, side elevational, and perspective views, respectively, of another embodiment of the invention with said embodiment shown in a relaxed state (FIGS. 20A and 20B) and compressed state (FIG. 20C).
Figure 20B:
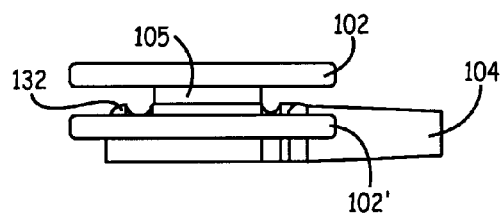
Figure 20C:
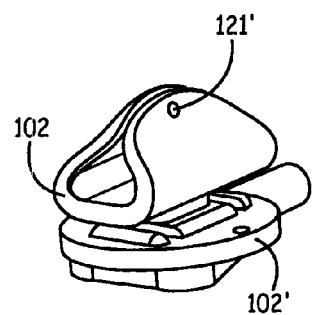

FIGS. 20A, 20B, and 20C are perspective, side, and perspective views, respectively, of another embodiment of an active pericardial fixation apparatus 100 according to the invention. The apparatus 100 is depicted in both a relaxed state (FIGS. 20A and 20B) and compressed state (FIG. 20C). In FIG. 20A, which resembles the embodiment depicted in FIG. 16A-16B except that member 102 is configured as a substantially round member and roughly corresponds in size and shape to the enlarged portion of body 101 (denoted as 102'). The enlarged portion 102' includes optional raised interlocking members 132 and 136 which tend to retain pericardial tissue disposed intermediate member 102 and portion 102' when implantation is complete according to the invention.

Figure 21A:
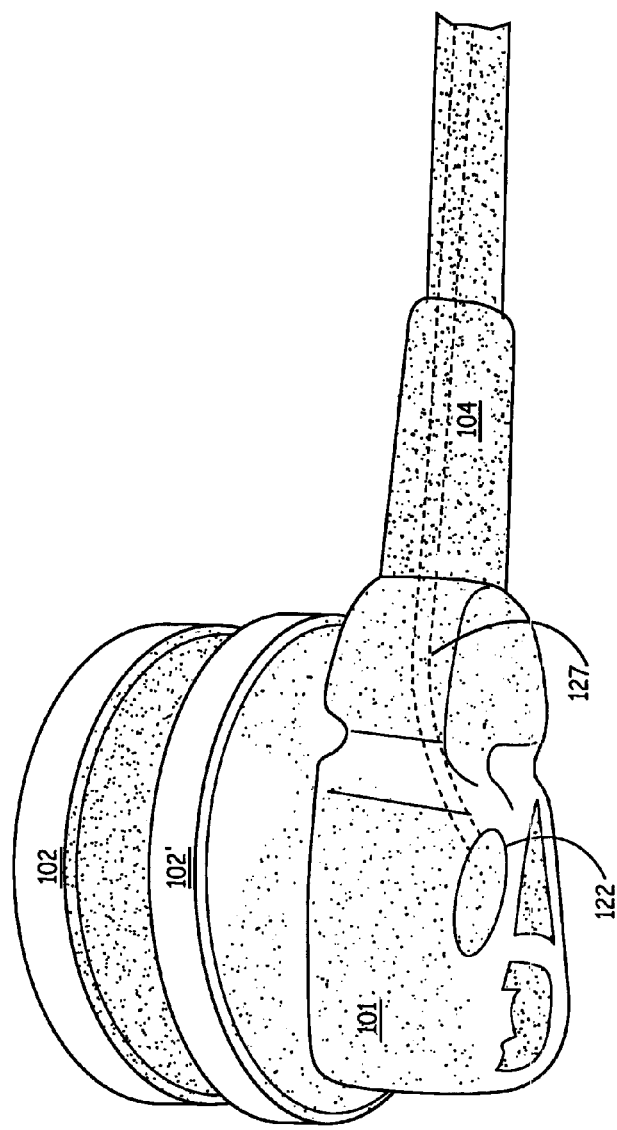
FIGS. 21A-21B are perspective photographic views depicting a related form of the active pericardial fixation apparatus according to the embodiment of the invention depicted in FIGS. 20A, 20B, and 20C.
Figure 21B:
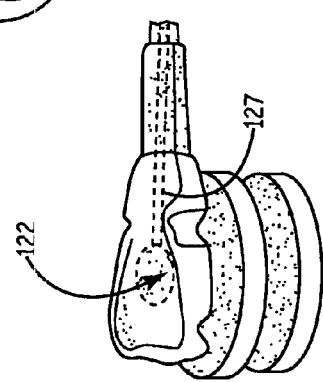

FIGS. 21A-21B are perspective photographic views depicting a related form of the active pericardial fixation apparatus 100 substantially according to the embodiment of the invention depicted in FIGS. 20A, 20B, and 20C. As shown in FIG. 21A the apparatus is in a relaxed state (i.e., member 102 and enlarged portion 102' are substantially parallel). The electrode-and/or sensor-receiving location 122 is depicted as residing upon the epicardium-contacting side of body 101 and couples to an elongated conductor 127 (shown in ghost) extending through the body 101 and through the lead 104. In FIG. 21B, the location 122 is depicted in ghost as a location within body 101 with conductor 127 extending therefrom. As mentioned elsewhere herein, diverse electrode-and/or sensor-receiving locations can be implemented according to the invention, including locations within and/or upon a surface portion of any part of apparatus 100 including the lead 104, the body 101, the member 102, the enlarged portion 102', etc.

Figure 22A:
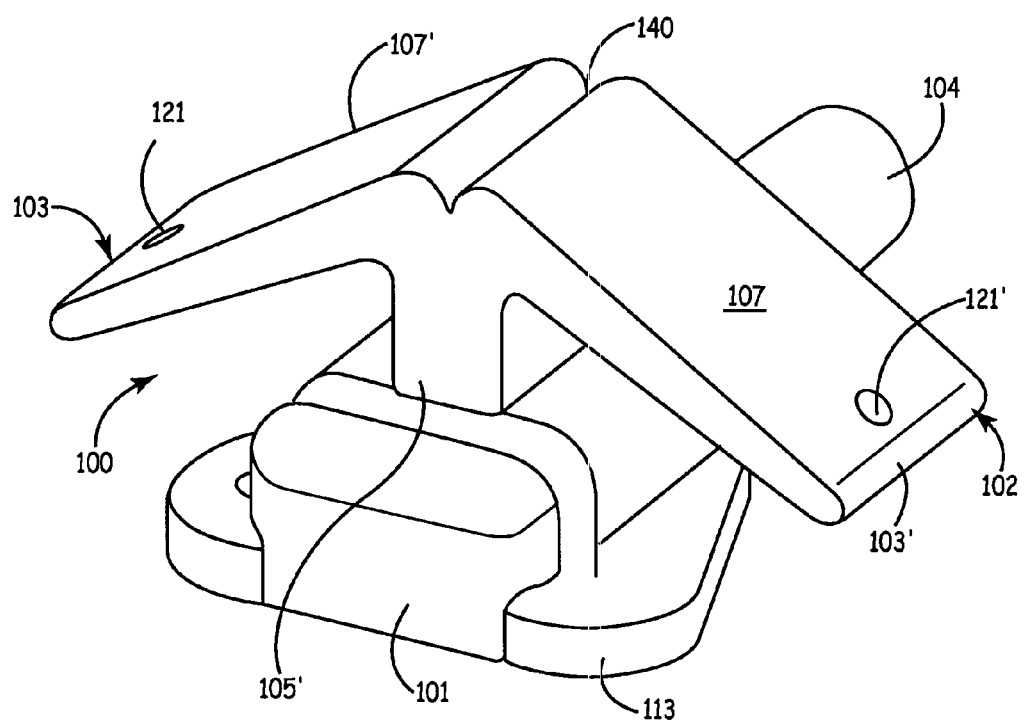
FIGS. 22A and 22B are perspective views depicting certain aspects of one form an active pericardial fixation apparatus according to the invention wherein said apparatus is shown in a relaxed state and a compressed state, respectively.
Figure 22B:
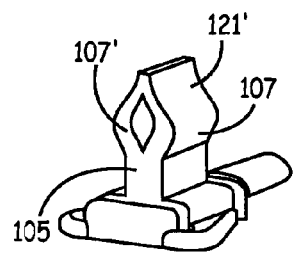

FIGS. 22A and 22B are perspective views depicting certain aspects of one form an active pericardial fixation apparatus 100 according to the invention wherein said apparatus 100 is shown in a relaxed state and a compressed state, respectively. In this embodiment the member 102 includes two different major surfaces 107,107' each having an end 103,103' and apertures 121,121', respectively. A connecting portion 105' couples the member 102 to the body 101. Referring now to FIG. 22B, the apparatus 100 is shown in the compressed state wherein the apertures 121,121' are brought together (e.g., with a wire, tool, cordage, etc.—not shown) to promote easier passage through an incision in the pericardium substantially as previously described.

Figure 23:
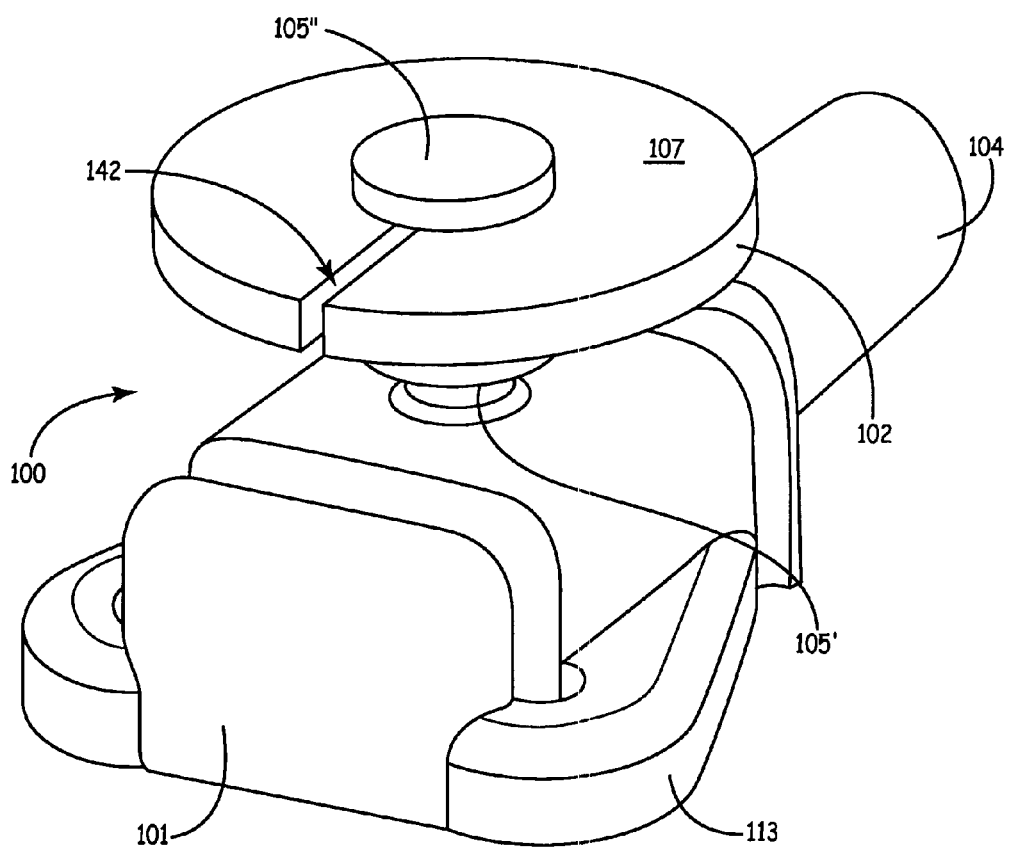
FIG. 23 is a perspective view of yet another embodiment of the present invention.

FIG. 23 is a perspective view of yet another embodiment of an active fixation apparatus 100 according to the present invention. In this embodiment the fixation member 102 has a slot 142 extending to a central region of the member 102 and sized to receive a distal portion of the connector 105' that connects to body 101. Thus, the member 102 can be twisted or manipulated to open the slot 142 and engaged upon the connector 105' intermediate an enlarged end portion 105". The end portion 105" can be integral with connector 105' or can comprise a cap member suitably attached to the connector 105'. Thus following deployment of the apparatus 100 of FIG. 23 the fixation member 102 can be attached to the connector 105' following the emergence of end portion 105" from a pericardial incision thereby not requiring transition between a compressed and relaxed state.

Figure 24:
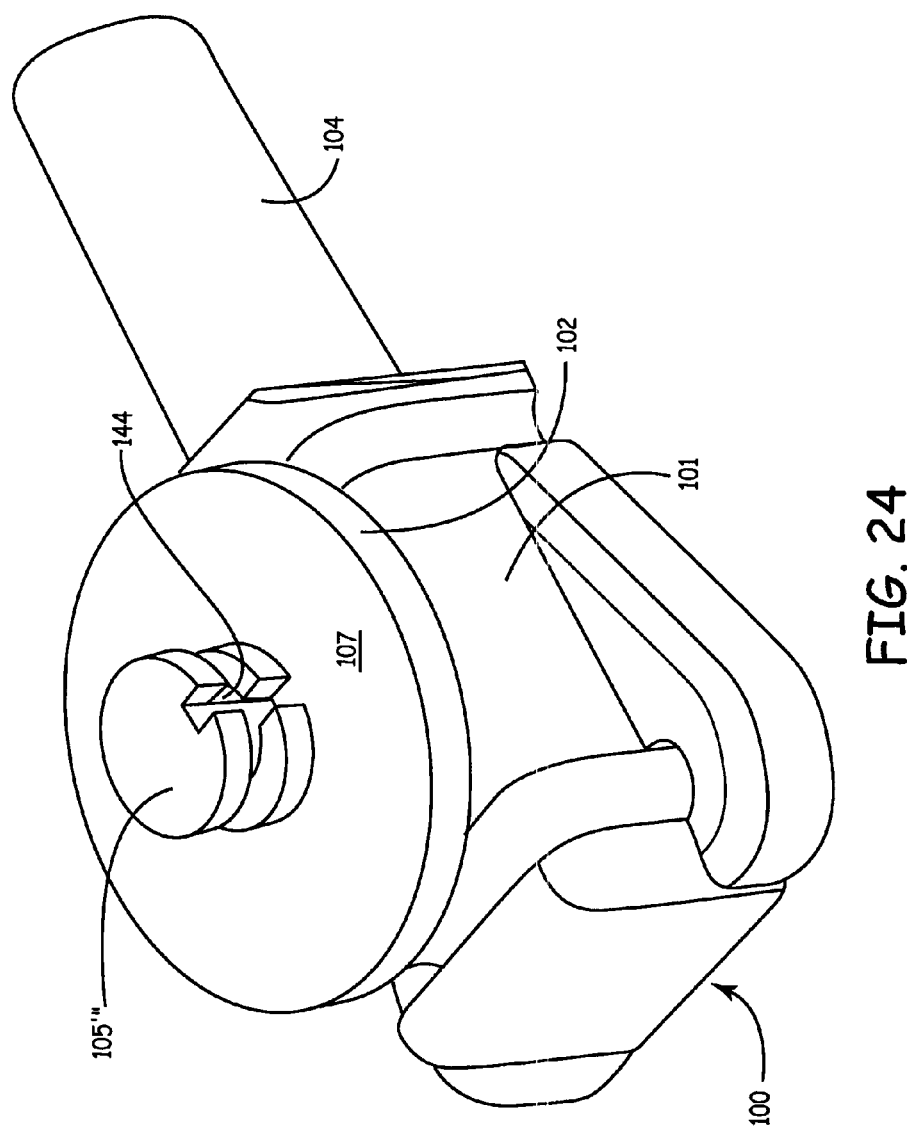
FIG. 24 is a perspective view of an embodiment of the present invention that is related to that depicted in FIG. 23.

FIG. 24 is a perspective view of an embodiment of the fixation apparatus 100 according to the present invention that relates to the embodiment depicted in FIG. 23. In this embodiment, the fixation member 102 couples to the body 101 with a cam member 105'" that includes an axial slot 144 that positively mechanically interlocks with corresponding structure surrounding an aperture of the member 102. The cam member 105'" can be integral with the connector (105'—not shown) or can be coupled to connector 105' following emergence of the connector following emergence from an incision in the pericardium. In any event, once exposed through the incision the fixation member 102 is coupled to the cam member 105'" and rotated into positive engagement thereto thus providing positive biasing forces to pericardial tissue disposed between body 101 and member 102.

Figure 25:
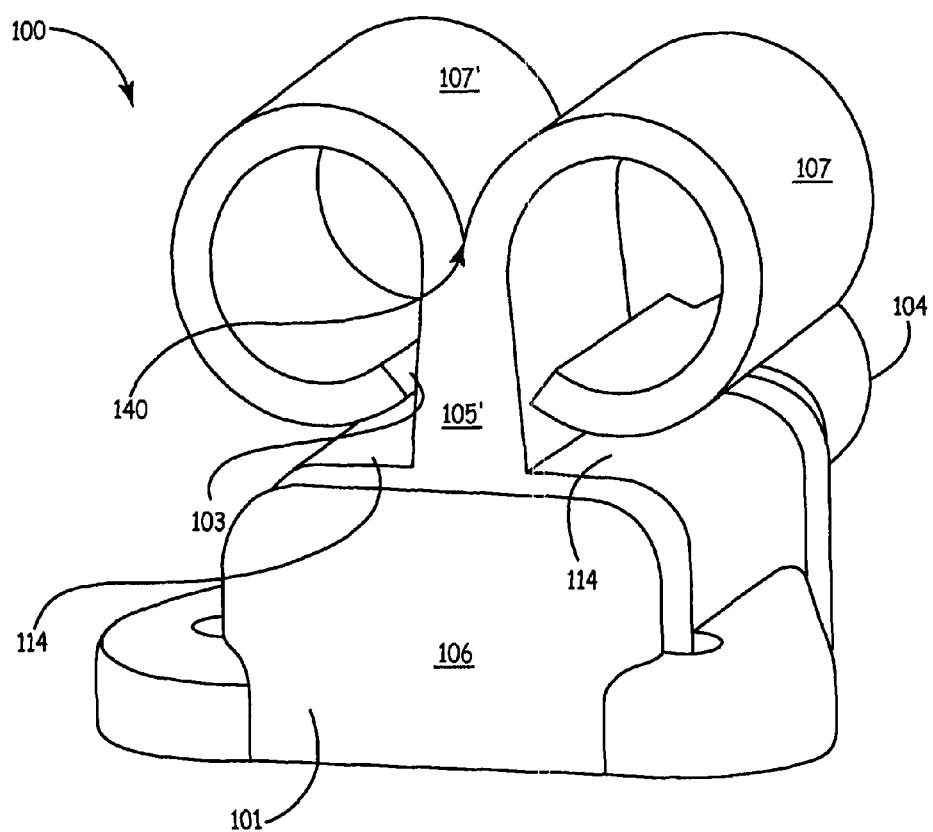
FIG. 25 is a perspective view of another related embodiment of the present invention including active mechanical fixation according to another aspect of the present invention.

FIG. 25 is a perspective view of another related embodiment of the present invention including active mechanical fixation apparatus 100 according to another aspect of the present invention. In this embodiment, the member 102 comprises two discrete major curvilinear surfaces 107,107' separated by a narrow slot 140 disposed at a distal end of connector 105'. Each major surface 107,107' terminates at an end 103 and defines a resilient loop of material each having a portion closely spaced from surface 114 of the body 101. It is in this location that the pericardium impinges upon by the positive biasing forces produced by the surfaces 107,107' that comprise the flexible member 102 thereby providing the positive fixation as previously described with respect to other embodiments of the present invention.

In the foregoing detailed description, the invention has been described with reference to specific embodiments. However, it may be appreciated that various modifications and changes can be made without departing from the scope of the invention as set forth in the appended claims.

The invention claimed is:

1. A method of operatively deploying an implantable medical component into a fixed position within pericardial tissue, comprising:

incising through a first portion of pericardial tissue and a second portion of pericardial tissue, wherein the incising forms an incised edge in the second portion of the pericardial tissue;

advancing an implantable medical component through the first portion of pericardial tissue into the pericardial space, wherein the implantable medical component comprises a body structure and a fixation member coupled to the body structure, wherein the fixation member extends over a pericardial sac-contacting side of the body structure; and fixating the implantable medical component to the second portion of pericardial tissue by locating the incised edge of the pericardial sac between the fixation member and the pericardial sac-contacting side of the body structure, wherein the fixation member and the body structure generate a biasing force between the fixation member and the pericardial sac-contacting side of the body structure, and wherein a portion of the fixation member is disposed external to the second portion of pericardial tissue and a portion of the implantable medical component is disposed internal to the second portion of pericardial tissue when the incised edge of the pericardial sac is located between the fixation member and the pericardial sac-contacting side of the body structure.

2. A method according to claim 1, wherein the body structure comprises a physiologic sensor.

3. A method according to claim 2, wherein the physiologic sensor comprises a pressure sensor.

4. A method according to claim 2, wherein the physiologic sensor comprises a metabolic sensor.

5. A method according to claim 2, wherein the physiologic sensor comprises an accelerometer.

6. A method according to claim 1, wherein the fixation member comprises a resilient member and said resilient member is configured as a curvilinear member.

7. A method according to claim 1, wherein the body structure comprises a cardiac pacing/sensing electrode.

8. A method according to claim 1, wherein the body structure comprises a cardiac defibrillation electrode.

9. A method according to claim 1, wherein the fixation member comprises a resilient member and said resilient member is configured as a substantially planar member.

10. A method according to claim 1, wherein the fixation member comprises a resilient member and said resilient member is configured as a spaced-apart pair of substantially planar members.

11. A method according to claim 1, wherein the fixation member comprises a resilient member and said resilient member is configured as a member having a relaxed state and a compressed state.

12. A method of operatively deploying an implantable medical component into a fixed position within pericardial tissue, comprising:
    incising through a first portion of pericardial tissue and a second portion of pericardial tissue, wherein the incising forms an incised edge in the second portion of the pericardial tissue;
    advancing an implantable medical component through the first portion of pericardial tissue into the pericardial space, wherein the implantable medical component comprises a body structure and a fixation member coupled to the body structure, wherein the fixation member extends over a pericardial sac-contacting side of the body structure, and wherein the body structure comprises at least one of a cardiac pacing/sensing electrode and a cardiac defibrillation electrode, and wherein the fixation member comprises a resilient member and said resilient member is configured as a substantially planar member; and
    fixating the implantable medical component to the second portion of pericardial tissue by locating the incised edge of the pericardial sac between the fixation member and the pericardial sac-contacting side of the body structure, wherein the fixation member and the body structure generate a biasing force between the fixation member and the pericardial sac-contacting side of the body structure, and wherein a portion of the fixation member is disposed external to the second portion of pericardial tissue and a portion of the implantable medical component is disposed internal to the second portion of pericardial tissue when the incised edge of the pericardial sac is located between the fixation member and the pericardial sac-contacting side of the body structure.

13. A method according to claim 12, wherein the body structure comprises a physiologic sensor.

14. A method according to claim 13, wherein the physiologic sensor comprises a pressure sensor.

15. A method according to claim 13, wherein the physiologic sensor comprises a metabolic sensor.

16. A method according to claim 13, wherein the physiologic sensor comprises an accelerometer.

17. A method of operatively deploying an implantable medical component into a fixed position within pericardial tissue, comprising:
    incising through a first portion of pericardial tissue and a second portion of pericardial tissue, wherein the incising forms an incised edge in the second portion of the pericardial tissue;
    advancing an implantable medical component through the first portion of pericardial tissue into the pericardial space, wherein the implantable medical component comprises a body structure and a fixation member coupled to the body structure, wherein the fixation member extends over a pericardial sac-contacting side of the body structure, and wherein the body structure comprises at least one of a cardiac pacing/sensing electrode and a cardiac defibrillation electrode, and wherein the fixation member comprises a resilient member and said resilient member is configured as a member having a relaxed state and a compressed state; and
    fixating the implantable medical component to the second portion of pericardial tissue by locating the incised edge of the pericardial sac between the fixation member and the pericardial sac-contacting side of the body structure, wherein the fixation member and the body structure generate a biasing force between the fixation member and the pericardial sac-contacting side of the body structure, and wherein a portion of the fixation member is disposed external to the second portion of pericardial tissue and a portion of the implantable medical component is disposed internal to the second portion of pericardial tissue when the incised edge of the pericardial sac is located between the fixation member and the pericardial sac-contacting side of the body structure.

18. A method according to claim 17, wherein the body structure comprises a physiologic sensor.

19. A method according to claim 18, wherein the physiologic sensor comprises a pressure sensor.

20. A method according to claim 18, wherein the physiologic sensor comprises a metabolic sensor.

21. A method according to claim 18, wherein the physiologic sensor comprises an accelerometer.

* * * * *